(12) United States Patent
Nair et al.

(10) Patent No.: US 11,242,401 B2
(45) Date of Patent: Feb. 8, 2022

(54) MONOCLONAL ANTIBODY AND A METHOD OF USE FOR THE TREATMENT OF LUPUS

(71) Applicant: Biocon Limited, Bangalore (IN)

(72) Inventors: Pradip Nair, Bangalore (IN); Ravindra Belavinakodige Sadashivarao, Karnataka (IN); Ramakrishnan Melarkode, Bangalore (IN)

(73) Assignee: BIOCON LIMITED

( * ) Notice: Subject to any disclaimer, the term of this patent is extended or adjusted under 35 U.S.C. 154(b) by 0 days.

(21) Appl. No.: 16/343,127

(22) PCT Filed: Oct. 17, 2017

(86) PCT No.: PCT/IB2017/056428
§ 371 (c)(1),
(2) Date: Apr. 18, 2019

(87) PCT Pub. No.: WO2018/073734
PCT Pub. Date: Apr. 26, 2018

(65) Prior Publication Data
US 2019/0241670 A1 Aug. 8, 2019

(30) Foreign Application Priority Data
Oct. 21, 2016 (IN) .............................. 201641036145

(51) Int. Cl.
| | | |
|---|---|---|
| C07K 16/28 | (2006.01) | |
| A61K 39/395 | (2006.01) | |
| C07K 16/18 | (2006.01) | |
| A61P 37/06 | (2006.01) | |
| A61P 37/04 | (2006.01) | |
| A61K 45/06 | (2006.01) | |
| A61K 39/00 | (2006.01) | |

(52) U.S. Cl.
CPC ........ *C07K 16/2896* (2013.01); *A61K 39/395* (2013.01); *A61K 39/39541* (2013.01); *A61K 45/06* (2013.01); *A61P 37/04* (2018.01); *A61P 37/06* (2018.01); *C07K 16/18* (2013.01); *A61K 2039/505* (2013.01); *C07K 2317/73* (2013.01); *C07K 2317/732* (2013.01)

(58) Field of Classification Search
None
See application file for complete search history.

(56) References Cited

U.S. PATENT DOCUMENTS

| | | | |
|---|---|---|---|
| 699,755 | A | 5/1902 | Hoag |
| 5,604,209 | A | 2/1997 | Ubasawa et al. |
| 5,712,120 | A | 1/1998 | Rodriguez et al. |
| 5,998,172 | A | 7/1999 | Haynes et al. |
| 6,162,432 | A | 12/2000 | Wallner et al. |
| 6,221,907 | B1 | 4/2001 | Balasubramanian |
| 6,267,958 | B1 | 7/2001 | Andya et al. |
| 6,372,215 | B1 | 4/2002 | Starling et al. |
| 6,572,857 | B1 | 6/2003 | Casimiro et al. |
| 7,728,114 | B2 | 6/2010 | Mach et al. |
| 8,435,521 | B2 | 5/2013 | Casimiro et al. |
| 8,524,233 | B2 * | 9/2013 | Melarkode ................ A61P 7/00 424/144.1 |
| 9,217,037 | B2 | 12/2015 | Melarkode et al. |
| 9,670,285 | B2 | 6/2017 | Melarkode et al. |
| 10,000,573 | B2 * | 6/2018 | Melarkode .............. A61P 43/00 |
| 11,028,168 | B2 | 6/2021 | Nair et al. |
| 2002/0187526 | A1 | 12/2002 | Ruben et al. |
| 2003/0113316 | A1 | 6/2003 | Kaisheva et al. |
| 2004/0091490 | A1 | 5/2004 | Johnson et al. |
| 2004/0197324 | A1 | 10/2004 | Liu et al. |
| 2006/0173170 | A1 | 8/2006 | Chamberlain et al. |
| 2006/0210557 | A1 | 9/2006 | Luisi et al. |
| 2007/0086979 | A1 | 4/2007 | Chevrier et al. |
| 2010/0047242 | A1 | 2/2010 | Casimiro et al. |
| 2010/0092423 | A1 | 4/2010 | Casimiro et al. |
| 2010/0166767 | A1 | 7/2010 | Presta |
| 2011/0002939 | A1 | 1/2011 | Melarkode et al. |
| 2012/0231009 | A1 | 9/2012 | Ramini et al. |
| 2014/0031529 | A1 | 1/2014 | Melarkode et al. |
| 2016/0024220 | A1 | 1/2016 | Casimiro et al. |
| 2016/0152705 | A1 | 6/2016 | Nair et al. |
| 2016/0168256 | A1 | 6/2016 | Melarkode et al. |
| 2017/0066835 | A1 | 3/2017 | Casimiro et al. |
| 2017/0281808 | A1 | 10/2017 | Melarkode et al. |
| 2017/0362331 | A1 | 12/2017 | Lin |
| 2018/0258179 | A1 | 9/2018 | Melarkode et al. |
| 2019/0248913 | A1 | 8/2019 | Nair et al. |

(Continued)

FOREIGN PATENT DOCUMENTS

| | | |
|---|---|---|
| CN | 101199483 B | 1/2011 |
| CN | 102559636 B | 3/2014 |

(Continued)

OTHER PUBLICATIONS

Imran et al., Clin Exp Nephrol (2016) 20:1-13. (Year: 2016).*
Furie et al. (Semin Nephrol. Sep. 2015;35(5):509-20). (Year: 2015).*
Roccatello et al., Autoimmunity Reviews 14 (2015) 1123-1130. (Year: 2015).*
Wu et al., The Journal of Immunology, 2010, 184: 2183-2193. (Year: 2010).*
Orme et al., Clinical Immunology 169 (2016) 58-68. (Year: 2016).*
"Biocon Receives Marketing Authorization for its Novel Biologic Itolizumab for Psoriasis." www.pharmachat.com/biocon-receives-marketing-authorization-for-its-novel-biologic-itolizumab-for-psoriasis/, Jan. 8, 2013, 3 pages, http://www.pharmachitchat.com/biocon-receives-marketing-authorization-for -its-novel-biologic-itolizumab-for-psoriasis/.

(Continued)

*Primary Examiner* — Zachary S Skelding
(74) *Attorney, Agent, or Firm* — Cooley LLP

(57) ABSTRACT

The present invention relates to compositions and methods useful for the treatment of lupus using a humanized IgG1 anti-CD6 monoclonal antibody (T1h) that binds to the SRCR domain 1 (D1) of CD6 without blocking the interaction of CD6 with the CD6 ligand Activated Leukocyte Cell Adhesion Molecule (ALCAM).

7 Claims, 15 Drawing Sheets
Specification includes a Sequence Listing.

(56) References Cited

U.S. PATENT DOCUMENTS

| | | |
|---|---|---|
| 2019/0321285 A1 | 10/2019 | Ramini et al. |
| 2019/0345247 A1 | 11/2019 | Nair et al. |

FOREIGN PATENT DOCUMENTS

| | | | |
|---|---|---|---|
| EP | 0699755 A2 | 3/1996 | |
| EP | 0807125 A2 | 11/1997 | |
| EP | 0807125 B1 | 10/2004 | |
| EP | 2119452 A1 | 11/2009 | |
| ES | 2192128 | 9/2003 | |
| ES | 2254174 T3 | 6/2006 | |
| WO | WO 1995/012614 A1 | 5/1995 | |
| WO | WO 1997/004801 A1 | 2/1997 | |
| WO | WO 1997/019111 A2 | 5/1997 | |
| WO | WO 1998/003551 A1 | 1/1998 | |
| WO | WO 1998/043089 A1 | 10/1998 | |
| WO | WO 1998/047531 A2 | 10/1998 | |
| WO | WO 2000/067796 A1 | 11/2000 | |
| WO | WO 2001/070984 A2 | 9/2001 | |
| WO | WO 2001/091793 A1 | 12/2001 | |
| WO | WO 2005/080432 A2 | 9/2005 | |
| WO | WO 2007/147001 A2 | 12/2007 | |
| WO | WO 2008/071394 A1 | 6/2008 | |
| WO | WO 2008/077355 A1 | 7/2008 | |
| WO | WO 2008/077356 A1 | 7/2008 | |
| WO | WO 2008/086395 A2 | 7/2008 | |
| WO | WO 2008/157409 A1 | 12/2008 | |
| WO | WO 2009/002521 A2 | 12/2008 | |
| WO | WO 2009/037190 A2 | 3/2009 | |
| WO | WO 2009/113083 A1 | 9/2009 | |
| WO | WO 2011/061712 A1 | 5/2011 | |
| WO | WO 2015/011658 A1 | 1/2015 | |
| WO | WO-2015011660 A1 * | 1/2015 | ......... C07K 16/2896 |
| WO | WO 2018/073734 A1 | 4/2018 | |
| WO | WO 2019/169015 A1 | 9/2019 | |

OTHER PUBLICATIONS

Adhya et al., "The role of cytokines as biomarkers in systemic lupus erythematosus and lupus nephritis," Nephrol Dial Transplant. 2011, 26(10):3273-3280.

Aira et al., "Immunological and histological evaluation of clinical samples from psoriasis patients treated with anti-CD6 itolizumab," MAbs, May 1, 2014, vol. 6, Issue 3, pp. 782-792.

Alonso, et al., "Towards the Definition of a Chimpanzee and Human Conserved CD6 Domain 1 Epitope Recognized by T1 Monoclonal Antibody." Hybridoma (2008); 27(4): 291-301.

Alonso-Ramirez, Ruby et al., "Rationale for Targeting CD6 as a Treatment for Autoimmune Diseases." Arthritis (2010); 89(8): 1-9.

Annunziata, Francesco et al., "Phenotypic and functional features of human Th 17 cells." J Exp Med (2007); 204(8): 1849-1861.

Aranami, et al., "Th 17 Cells and Autoimmune Encephalomyelitis (EAE/MS)." Allergology International (2008); 57 (2): 115-120.

Aruffo, Alejandro et al. "CD6-ligand interactions: a paradigm for SRCR domain function?" Immunol. Today (1997), vol. 18, No. 10, pp. 498-504.

Aruffo et al., "The Lymphocyte Glycoprotein CD6 Contains a Repeated Domain Structure Characteristic of a New Family of Cell Surface and Secreted Proteins," J. Exp. Med. 1991, 174:949-952.

Aulton, et al., Pharmaceutics: The Science of Dosage Form Design, 2nd Ed., pp. 276-288 (2001).

Barr, et al., "B cell depletion therapy ameliorates autoimmune disease through ablation of IL-6-producing B cells." J Exp Med. (2012); 209(5): 1001-1010.

Bettelli, Estelle et al., "Induction and effector functions of TH 17 cells." Nature 2008, 453(7198): 1051-7.

Blank et al., "Experimental models of systemic lupus erythematosus: anti-dsDNA in murine lupus," Rheumatology 2005;44:1086-1089.

Bott et al., "Activation of human T cells through CD6: functional effects of a novel anti-CD6 monoclonal antibody and definition of four epitopes of the CD6 glycoprotein," Int. Immunol. 1993, 5(7):783-792.

Bowen et al., "Cloning, Mapping, and Characterization of Activated Leukocyte-Cell Adhesion Molecule (ALCAM), a CD6 Ligand," J. Exp. Med 1995, 181:2213-2220.

Browning, Jeffrey L. "B cells move to centre stage: novel opportunities for autoimmune disease treatment." Nature Reviews Drug Discovery (2006) vol. 5, pp. 564-576.

Brucklacher-Waldert, Verena et al. "Phenotypical and functional characterization of T helper 17 cells in multiple sclerosis." Brain (2009); 132(Pt 12): 3329-3341.

Cardenas et al., "Phosphorylation-dephosphorylation of the CD6 glycoprotein renders two isoforms of 130 and 105 kilodaltons. Effect of serum and protein kinase C activators," J. Immunol. 1990, 145(5):1450-1455.

Cheifetz, Adam et al., "The Incidence and Management of Infusion Reactions to Infliximab: A Large Center Experience." The American Journal of Gastroenterology, (2003) vol. 98, No. 6, pp. 1315-1324.

Chen et al., "Inhibition of TFGβ1 by Anti-TFGβ1 Antibody or Lisinopril Reduces Thyroid Fibrosis m Granulomatous Experimental Autoimmune Thyroiditis." J Immunol. Dec. 1, 2002; 169(11):6530-6538.

Cleland, Jeffrey L. et al., "A Specific Molar Ratio of Stabilizer to Protein is Required for Storage Stability of a Lyophilized Monoclonal Antibody." Journal of Pharmaceutical Sciences, Mar. 2001, vol. 90, No. 3, pp. 310-321.

Chopra, et al., "Itolizumab in combination with methotrexate modulates active rheumatoid arthritis: safety and efficacy from a phase 2, randomized, open-label, parallel-group, dose-arranging study." Clinical Rheumatology (2016); 35(4): 1059-1064. Epub Jun. 7, 2015.

Croxford, Andrew L. et al., "IL-23 One cytokine in control of autoimmunity." European Journal of Immunology (2012); 42(9): 2263-2273.

De Wit, Jelle, et al., "CDS costimulation induces stable Th 17 development by promoting IL-23R expression and sustained STAT3 activation." Blood (2011);118(23): 6107-6114.

Den Broeder, Alfons et al., "A Single Dose, Placebo Controlled Study of the Fully Human Anti-Tumor Necrosis Factor-a Antibody Adalimumab (D2E7) in Patients with Rheumatoid Arthritis." The Journal of Rheumatology (2002) vol. 29, No. 11, pp. 2288-2298.

Dick, et al., "Secukinumab in the Treatment of Noninfectious Uveitis: Results of Three Randomized, Controlled Clinical Trials." Ophthalmology (2013); 120(4): 777-787.

Dillman, "Monoclonal antibodies for treating cancer." Annals of Internal Medicine (1989); 111:592-603.

Edwards, Jonathan C.W. et al., "Efficacy of B-Cell-Targeted Therapy with Rituximab in Patients with Rheumatoid Arthritis." The New England Journal of Medicine (2004) vol. 350, pp. 2572-2581.

Extended European Search Report, corresponding to European Patent Application No. 10831248.9, dated Sep. 8, 2014.

Feldmann, Marc et al., "Design of effective immunotherapy for human autoimmunity." Nature (2005) vol. 435, pp. 612-619.

Forrester, et al., "Uveitis in Mouse and Man." International Reviews of Immunology (2013); 32(1): 76-96.

Fuss et al., "Nonclassical CD1d-restricted NK T cells that produce IL-13 characterize an atypical Th2 response in ulcerative colitis." The Journal of Clinical Investigation, vol. 113 No. 10, May 2004, p. 1490-1497.

Gaffen, Sarah L., "Role of IL-17 in the Pathogenesis of Rheumatoid Arthritis." 2009, Current Rheumatology Rep. 11 :5:365-370.

Gangemi et al., "Anti-T12, an anti-CD6 monoclonal antibody, can activate human T lymphocytes," J. Immunol. 1989, 143:2439-2447.

Garber, Ken., "First-in-class biologic to enter rheumatoid arthritis fray." Nature (2005) vol. 23, No. 11, pp. 1323-1324.

Garcia, et al., "Phase I clinical trial of IOR-T1 monoclonal antibody in T lymphoma: pharmacokinetics and immune response." Cuban Journal of Medicine, v. 42, No. 2, 2003, pp. 1-7, Google automated English language translation of Spanish original).

Garcia, et al., Cuban Journal of Medicine, v. 42, No. 2, 2003, pp. 1-7, Spanish language document.

Gimferrer et al., "Relevance of CD6-Mediated Interactions in T Cell Activation and Proliferation," J Immunol 2004, 173: 2262-2270.

Goldblatt, F., et al. "New therapies for rheumatoid arthritis." Clinical and Experimental Immunology (2005) vol. 140, pp. 195-204.

Goldsby, et al., Immunology, 2003, Freeman Press, pp. 290-291.

(56) References Cited

OTHER PUBLICATIONS

Hale, Douglas A., "Biological effects of induction immunosuppression." Current Opinion in Immunology (2004) vol. 16, pp. 565-570.
Harrison, P.V. et al., "Short-term methotrexate administration by low-dose-infusion does it influence clearance of psoriasis?" Clinical and Experimental Dermatology (1989) vol. 14, pp. 291-294.
Hassan et al., "CD6 Regulates T-Cell Responses through Activation-Dependent Recruitment of the Positive Regulator SLP-76", Molecular and Cellular Biology, 2006, vol. 26, Issue 17, pp. 6727-6738.
Heldin et al., "Dimerization of Cell Surface Receptors in Signal Transduction." Cell. Jan. 27, 1995; 80(2):213-233.
Hernández, et al., "Therapeutic Targeting of CD6 in Autoimmune Diseases: A Review of Cuban Clinical Studies with the Antibodies IOR-T1 and Itolizumab." Current Drug Targets (2016); 17(6): 1-12.
Heydendael, Vera M.R et al., "Methotrexate versus Cyclosporine in Moderate to-Severe Chronic Plague Psoriasis." The New England Journal of Medicine (2003) vol. 349, pp. 658-665.
Horwitz et al., "Decreased Production of Interleukin-12 and Other Th1-Type Cytokines in Patients with Recent-Onset Systemic Lupus Erythematosus." Arthritis Rheum. May 1998;41(5): 838-844.
Ibáñez, et al., "Mitogen-Activated Protein Kinase Pathway Activation by the CD6 Lymphocyte Surface Receptor." Journal of Immunology, Jul. 2006, vol. 177(2): 1152-1159.
International Preliminary Report on Patentability for International Application No. PCT/IB2010/055296, dated May 20, 2012, 4 pages.
International Preliminary Report on Patentability for International Application No. PCT/IB2014/063345, dated Jan. 26, 2016, 7 pages.
International Preliminary Report on Patentability for International Application No. PCT/IN2008/000562, dated May 27, 2010, 10 pages.
International Preliminary Report on Patentability in International Application No. PCT/CU2007/000021, dated Oct. 6, 2009, and English translation, 24 pages.
International Preliminary Report on Patentability, and English translation, for International Application No. PCT/CU2007/000022, dated Oct. 6, 2009, 20 pages.
International Search Report and Written Opinion for International Application No. PCT/IB2010/055296, dated Mar. 4, 2011, 11 pages.
International Search Report and Written Opinion for International Application No. PCT/IB2014/063345, dated Nov. 18, 2014, 9 pages.
International Search Report and Written Opinion for International Application No. PCT/IN2008/000562, dated Mar. 4, 2009, 10 pages.
International Search Report for International Application No. PCT/CU2007/000022, dated Apr. 28, 2008, 4 pages.
International Search Report Written Opinion in International Application No. PCT/CU2007/000021, dated Apr. 21, 2008, and English translation, 22 pages.
International Search Report for International Application No. PCT/IB2017/056403, dated Feb. 6, 2018, 6 pages.
International Search Report for International Application No. PCT/IB2017/056428, dated Feb. 28, 2018, 4 pages.
Jadidi-Niaragh and Mirshafiey, "Th17 Cell, the New Player of Neuroinflammatory Process in Multiple Sclerosis." Scandinavian Journal of Immunology (2011); 74(1): 1-13.
Joo, et al., "Evidence for the Expression of a Second CD6 Ligand by Synovial Fibroblasts." Arthritis and Rheumatism (2000) vol. 43, No. 2, pp. 329-335.
Kahan, Barry D., "Individuality: the barrier to optimal immunosuppression." Nature Reviews Immunology (2003) vol. 3, pp. 831-838.
Kleinewietfeld, Marcus et al., "CCR6 expression defines regulatory effector/memory-like cells within the CD25(+)CD4+ T-cell subset." Blood (2005); 105(7): 2877-2886.
Krauss, et al., "Impact of antibody framework residue VH-71 on the stability of a humanised anti-MUC1 scFv and derived immunoenzyme." British Journal of Cancer (2004); 90: 1863-1870.

Kremer, Joel M. et al. "Treatment of Rheumatoid Arthritis with the Selective Costimulation Modulator Abatacept." Arthritis & Rheumatism (2005) vol. 52, No. 8, pp. 2263-2271.
Krupashankar DS et al., "Efficacy and safety of itolizumab, a novel anti-CD6 monoclonal antibody, in patients with moderate to severe chronic plaque psoriasis: results of a double-blind, randomized, placebo-controlled, phase-III study," J Am Acad Dermatol., Sep. 2014;71(3):484-492.
Larrick, J.W. and Gavilondo, J., "Meeting Report: Therapeutic antibody technology 97." Immunotechnology. Jan. 1998, vol. 3, pp. 303-307.
Le Dantec, Christelle et al. "Rationale for treating primary Sjogren's syndrome patients with an anti-CD6 monoclonal antibody (Itolizumab)." Immunol Res (2013); 56: 341-347.
Li et al., "Anti-DNA B Cells in MRL/Ipr Mice Show Altered Differentiation and Editing Pattern," J Exp Med, 2002, 196(12): p. 1543-52.
Liao, Fang et al., "CC-chemokine receptor 6 is expressed on diverse memory subsets of T cells and determines responsiveness to macrophage inflammatory protein 3 α." J Immunol (1999); 162(1): 186-194.
Liu et al., "Delineation of the Pathogenesis of Systemic Lupus Erythematosus by Using Murine Models," Adv Exp Med Biol, 2001. 490: p. 1-6.
Liu, Hong et al., "Regulation of IL-17 in human CCR6+ effector memory T cells." J Immunol (2008); 180(12): 7948-7957.
Liu et al., "The Expression of Th17-Associated Cytokines in Human Acute Graft-versus-Host Disease," Biol. Blood Marrow Transplant (2013) 19:1421-1429.
Marwaha, et al., "TH17 cells in autoimmunity and immunodeficiency: protective or pathogenic?" Frontiers In Immunology (2012); 3: 129, pp. 1-8.
Marian et al., "Treatment targets in systemic lupus erythematosus: biology and clinical perspective," Arthritis Research & Therapy, 2012, 14(Suppl 4):S3, 8 pages.
Mannoor et al., "Expression of Natural Autoantibodies in MRL-Ipr Mice Protects from Lupus Nephritis and Improves Survival," J Immunol. 2012, 188(8):3628-3638.
Mease, Philip, "Infliximab (Remicade) in the treatment of psoriatic arthritis." Therapeutic and Clinical Risk Management, 2006: 2(4), pp. 389-400.
Morimoto et al., "2H1—a novel antigen involved in T lymphocyte triggering," J. Immunol. 1988, 140(7):2165-2170.
Montero, E. et al. "Immunodiagnosis and therapeutic immunosuppression in rheumatoid arthritis with ior t1 (anti-CD6) monoclonal antibody." Arthritis Research, vol. 4, No. Suppl. 1, Abstracts of the 22nd European Workshop for Rheumatology Research, Arthritis Research, 2002, Abstract 114, 1 page.
Montero, E. et al., "Correspondence," Autoimmunity (1999); 29(2): 155-156.
Nair, et al., "The inhibition of T cell proliferation in a mixed lymphocyte reaction by Itolizumab (T1h) is associated with reduction in pro inflammatory cytokines and CD6 internalization. (52. 27)" The Journal of Immunology (2011); 186 (1 Supplement) (Meeting Abstract Supplement); http://www.jimmunol.org/content/186/1_Supplement/52.27.short.
Nair, P. et al., "CD6 synergistic co-stimulation promoting proinflammatory response is modulated without interfering with the activated leucocyte cell adhesion molecule interaction." Clin Exp Immunol (2010); 162(1): 116-130.
Normanton et al., "Current data on IL-17 and Th17 cells and implications for graft versus host disease," Einstein. 2013;11(2):237-46.
O'Dell, James R., "Therapeutic Strategies for Rheumatoid Arthritis." The New England Journal of Medicine (2004) vol. 350, pp. 2591-2602.
Oliveira, MI et al., "CD6 attenuates early and late signaling events, setting thresholds for T-cell activation," Eur. J. Immunol., 2012, 42: 195-205.
Olsen, Nancy J. et al. "New Drugs for Rheumatoid Arthritis." The New England Journal of Medicine (2004) vol. 350, pp. 2167-2179.

(56) References Cited

OTHER PUBLICATIONS

Orta-Mascaro, M et al., "CD6 modulates thymocyte selection and peripheral T cell homeostasis," J. Exp. Med., 2016, vol. 213, No. 8, pp. 1387-1397.
Osorio, et al., "CD6 ligation modulates the Bcl-2/Bax ratio and protects chronic lymphocytic leukemia B cells from apoptosis induced by anti-IgM." Blood (1997); 89(8): 2833-2841.
Osorio et al., "The Anti-CD6 mAb, IOR-T1, Defined a New Epitope on the Human CD6 Molecule That Induces Greater Responsiveness in T Cell Receptor/CD3-Mediated T Cell Proliferation," Cell. Immunol. 1994, 154:123-133.
Patel, D.D., "CD6" Journal of Biological Regulators and Homeostatic Agents (2000) vol. 14, No. 3, pp. 234-236.
Patel et al., "Identification and Characterization of a 100-kD Ligand for CD6 on Human Thymic Epithelial Cells," J. Exp. Med. 1995, 181:1563-1568.
Perry et al., "Murine Models of Systemic Lupus Erythematosus," J Biomed Biotechnol. 2011:271694, 19 pages.
Petermann, et al., "γδ T cells enhance autoimmunity by restraining regulatory T cell responses via an interleukin-23 dependent mechanism." Immunity (2011); 33(3): 351-363.
Pincus, T. et al., "Methotrexate as the "anchor drug" for the treatment of early rheumatoid arthritis." Clin Exp Rheumatol (2003) vol. 21 (Suppl 31) pp. S179-S185.
Pincus, Theodore et al., "Combination Therapy with Multiple Disease-Modifying Antirheumatic Drugs in Rheumatoid Arthritis: A Preventative Strategy." Ann Intern Med (1999) vol. 131, No. 10, pp. 768-774.
Pinto, Mafalda et al., "CD6 as a Therapeutic Target in Autoimmune Diseases: Successes and Challenges." Biodrugs (2013); 27(3): 191-202.
Poole et al., "Cytokines in systemic lupus erythematosus," J Biomed Biotechnol. 2010:735169, 2 pages.
Reddy, Manjula P. et al. "Elimination of F c Receptor-Dependent Effector Functions of a Modified IgG4 Monoclonal Antibody to Human CD4." The Journal of Immunology (2000) vol. 164, pp. 1925-1933.
Richards et al., Interleukin 6 dependence of anti-DNA antibody production: evidence for two pathways of autoantibody formation in pristane-induced lupus. J Exp Med, 1998. 188(5): p. 985-90.
Rodriguez, et al., "A clinical exploratory study with itolizumab, an anti-CD6 monoclonal antibody, in patients with rheumatoid arthritis." Results in Immunology (2012); 2: 204-211.
Roep et al., "Satisfaction (not) guaranteed: re-evaluating the use of animal models of type 1 diabetes." Nat Rev Immunol. Dec. 2004; 4(12): 989-997.
Roep, Bart, "Are Insights Gained from NOD Mice Sufficient to Guide Clinical Translation? Another Inconvenient Truth." Ann. N.Y. Acad. Sci. (2007); 1103: 1-10.
Roncagalli R, et al., "Quantitative proteomic analysis of signalosome dynamics in primary T cells identifies the CD6 surface receptor as a Lat-independent TCR signaling hub," Nature Immunology, 2014, vol. 15, Issue 4, pp. 384-392.
Roque-Navarro et al., "Humanization of Predicted T-Cell Epitopes Reduces the Immunogenicity of Chimeric Antibodies: New Evidence Supporting a Simple Method," Hybridoma and Hybridomics (2003), 22(4): 245-257.
Rostami, et al., "Role of Th17 cells in the pathogenesis of CNS inflammatory demyelination." Journal of Neurological Sciences (2013); 333 (1-2): 76-87.
Sallusto, Federica et al., "Flexible programs of chemokine receptor expression on human polarized T helper 1 and 2 lymphocytes." J Exp Med (1998); 187(6): 875-883.
Sanguine BioScience, "Types of immune cells present in human PBMC," Nov. 2012, 5 pages.
Schnyder, et al., "IL-17 reduces TNF-induced Rantes and VCAM-1 expression." Cytokine (2005); 31(3): 191-202.
Singer, N.G. et al., "CD6: expression during development, apoptosis and selection of human and mouse thymocytes." International Immunology, Jun. 2002, vol. 14, No. 6, pp. 585-597.

Smolen, Josef S. et al., "Therapeutic Strategies for Rheumatoid Arthritis." Nature Reviews Drug Discovery (2003) vol. 2, pp. 473-488.
Starling, Gary C. et al., "Characterization of mouse CD6 with novel monoclonal antibodies which enhance the allogeneic mixed leukocyte reaction." Eur. J. Immunol. 1996. 26:738-746.
Stohl and Looney, "B cell depletion therapy in systemic rheumatic diseases: Different strokes for different folks?" Clinical Immunology (2006), vol. 121. pp. 1-12.
Strober, Bruce E. et al., "Folate supplementation during methotrexate therapy for patients with psoriasis." Journal of American Dermatology (2005) vol. 53, No. 4, pp. 652-659.
Strom and Suthanthiran, "Therapeutic Approach to Organ Translation. Therapeutic Immunology" edited by Austen et al., Blackwell Science, Cambridge, MA, 1996; pp. 451-456.
Summons to attend Oral Proceedings, corresponding to European Patent Application No. 08873217.7, dated Feb. 6, 2015, 9 pages.
Swack et al., "Biosynthesis and Post-translational Modification of CD6, a T Cell Signal-transducing Molecule," J. Biol. Chem. 1991, 266(11):7137-7143.
Swack et al., "Structural characterization of CD6: properties of two distinct epitopes involved in T cell activation," Mol. Immunol. 1989 26:1037-1049.
Swierkot, Jerzy et al., "Methotrexate in rheumatoid arthritis." Pharmacological Reports (2006) vol. 58, pp. 473-492.
Taylor, Peter C. et al., "New approaches to therapeutic immunomodulation for immune-mediated inflammatory disorders." Current Opinion (2004); vol. 4, pp. 368-371.
The Biocon press release of Jun. 22, 2004, one page, http://www.biocon.com/biocon_press_archives_details.asp?subLink=news&Fileid=91, downloaded Feb. 15, 2013.
The Biocon press release of Nov. 30, 2006, one page, http://www.biocon.com/biocon_press_release_details.asp?subLink=news&Fileid=235, downloaded Feb. 15, 2013.
Theofilopoulos et al., "Murine models of systemic lupus erythematosus," Adv Immunol, 1985, 37:269-390.
Toussirot, Eric, "The IL23/Th17 Pathway as a Therapeutic Target in Chronic Inflammatory Diseases." Inflammation & Allergy (2012); 11(2): 159-168.
Wee et al., "Characterization of a CD6 Ligand(s) Expressed on Human- and Murine-Derived Cell Lines and Murine Lymphoid Tissues," Cell. Immunol. 1994, 158:353-364.
Wee et al., "Tyrosine Phosphorylation of CD6 by Stimulation of CD3: Augmentation by the CD4 and CD2 Coreceptors," J. Exp. Med. 1993, 177:219-223.
Whitney, et al., "The Membrane-proximal Scavenger Receptor Cysteine-rich Domain of CD6 Contains the Activated Leukocyte Cell Adhesion Molecule Binding Site," J. Biol. Chem. 1995, 270(31):18187-18190.
Written Opinion, and English translation, for International Application No. PCT/CU2007/000022, dated Apr. 28, 2008, 18 pages.
Yamazaki, Tomohide, et al., "CCR6 regulates the migration of inflammatory and regulatory T cells." J Immunol (2008); 181(12): 8391-401.
Youdim, Adrienne et al., "A Pilot Study of Adalimumab in Infliximab-Allergic Patients." Inflamm Bowel Dis (2004) vol. 10, No. 4 pp. 333-338.
Zimmerman, Aukje W. et al., "Long-term engagement of CD6 and ALCAM is essential for T-cell proliferation induced by dendritic cells." Blood (2006); 107(8): 3212-3220.
Biocon Annual Report 2013, Jul. 14, 2013, 189 pages.
Beck et al., "6th Annual European Antibody Congress 2010, Nov. 29-Dec. 1, 2010, Geneva, Switzerland," mAbs 3:2, 111-132; Mar./Apr. 2011.
Edwards, et al., "The Remarkable Flexibility of the Human Antibody Repertoire; Isolation of Over One Thousand Different Antibodies to a Single Protein, BLyS," J. Mol. Biol., (2003) 334, 103-118.
Harlow et al., eds., "Antibody Response," Antibodies: A Laboratory Manual, 1988, Chapter 4, pp. 37-47 and 55-59.
Heidt et al., "The impact of TH17 cells on transplant rejection and the induction of tolerance," Curr Opin Organ Transplant. Aug. 2010; 15(4): 456-461.

(56) References Cited

OTHER PUBLICATIONS

Lloyd et al., "Modelling the human immune response: performance of a 10 11 human antibody repertoire against a broad panel of therapeutically relevant antigens," Protein Engineering, Design & Selection, 2009, vol. 22, No. 3, pp. 159-168.

Meyer et al., "New insights in Type I and II CD20 antibody mechanisms-of-action with a panel of novel CD20 antibodies," British Journal of Haematology, 2018, 180, 808-82.

Seyedian et al., "A review of the diagnosis, prevention, and treatment methods of inflammatory bowel disease," Journal of Medicine and Life vol. 12, Issue 2, Apr.-Jun. 2019, pp. 113-122.

Consuegra-Fernández et al., "Clinical and experimental evidence for targeting CD6 in immune-based disorders," Autoimmunity Reviews, 2018, vol. 17, pp. 493-503.

Cosmi et al., "Th 17 cells: new players in asthma pathogenesis T lymphocytes and asthma phenotypes," Allergy, 2011, vol. 66, No. 8, pp. 989-998.

Der et al., "CD6-ALCAM Signaling Is Upregulated in Kidneys with Lupus Nephritis and Is Associated with Disease Activity," 2019 ACR/ARP Annual Meeting, Nov. 13, 2019, Abstract No. 2894, 3 pages, retrieved from https://acrabstracts.org/abstract/cd6-alcam-signaling-is-upregulated-in-kidneys-with-lupus-nephritis-and-is-associated-with-disease-activity/.

Galvez, J., "Role of Th 17 Cells in the Pathogenesis of Human IBD," ISRN Inflammation, 2014, vol. 2014, Article ID 928461, 14 pages.

Garner et al., "CD6 monoclonal antibodies differ in epitope, kinetics and mechanism of action," Immunology, 2018, 155, 273-282.

Granlund et al., "Whole Genome Gene Expression Meta-Analysis of Inflammatory Bowel Disease Colon Mucosa Demonstrates Lack of Major Differences between Crohn's Disease and Ulcerative Colitis," PLoS ONE (2013) 8(2): e56818, 13 pages.

Hundorfean et al., "Functional Relevance of T Helper 17 (Th 17) Cells and the IL-17 Cytokine Family in Inflammatory Bowel Disease," Inflamm Bowel Dis 2012;18:180-186.

International Search Report and Written Opinion for International Application No. PCT/US2019/019872, dated May 21, 2019, 4 pages.

International Search Report and Written Opinion for International Application No. PCT/US2020/019990, dated Jul. 15, 2020, 16 pages.

Jayaraman, K., "Biocon's first-in-class anti-CD6 mAb reaches the market," Nat. Biotechnol. 31, 1062-1063 (2013).

Schmidt et al., "TH17 Cell Induction and Effects of IL-17A and IL-17F Blockade in Experimental Colitis," Inflamm Bowel Dis, 2013, 19:1567-1576.

Waldman and Madaio, "Pathogenic autoantibodies in lupus nephritis," Lupus, 14:19-24, 2005.

Yang et al., "T cell-derived inducible nitric oxide synthase switches off TH17 cell differentiation," J. Exp. Med., 2013, vol. 210, No. 7, pp. 1447-1462.

\* cited by examiner

VH sequence:

GAAGTGCAGCTGGTGGAGTCTGGGGGAGGCTTAGTGAAGCCTGGAGGG
TCCCTGAAACTCTCCTGTGCAGCCTCTGGATTCAAGTTTAGTAGATATG
CCATGTCTTGGGTTCGCCAGGCTCCGGGGAAGAGGCTGGAGTGGGTCG
CAACCATTAGTAGTGGTGGTAGTTACATCTACTATCCAGACAGTGTGAA
GGGTCGATTCACCATCTCCAGAGACAATGTCAAGAACACCCTGTATCTG
CAAATGAGCAGTCTGAGGTCTGAGGACACGGCCATGTATTACTGTGCA
AGACGAGATTACGACCTGGACTACTTTGACTCCTGGGGCCAAGGCACC
CTTGTCACCGTCTCCTCA

Vk sequence:

GACATCCAGATGACCCAGTCTCCATCCTCCCTGTCTGCATCGGTGGGAG
ACAGAGTCACTATCACTTGCAAGGCGAGTCGGGACATTAGAAGCTATT
TAACCTGGTACCAGCAGAAACCAGGGAAAGCTCCTAAGACCCTGATCT
ATTATGCAACAAGCTTGGCAGATGGGGTCCCGTCGAGATTCAGTGGCA
GTGGATCTGGGCAAGATTATTCTCTCACCATCAGCAGCCTGGAGTCTGA
CGATACAGCAACTTACTACTGTCTACAACATGGTGAGAGTCCATTCACG
CTCGGCTCGGGGACCAAGCTGGAAATCAAA

Figure 7A

VH sequence:

EVQLVESGGGLVKPGGSLKLSCAASGFKFSRYAMSW
VRQAPGKRLEWVATISSGGSYIYYPDSVKGRFTISRD
NVKNTLYLQMSSLRSEDTAMYYCARRDYDLDYFDS
WGQGTLVTVSS

VK sequence:

DIQMTQSPSSLSASVGDRVTITCKASRDIRSYLTWYQ
QKPGKAPKTLIYYATSLADGVPSRFSGSGSGQDYSLT
ISSLESDDTATYYCLQHGESPFTLGSGTKLEIK

Figure 7B

DIQMTQSPSSLSASVGDRVTITCKASRDIRSYLTWYQQKP

DIQMTQSPSSLSASVGDRVTITCKASRDIRSYLTWYQQKP

DIQMTQSPSSLSASVGDRVTITCKASRDIRSYLTWYQQKP

GKAPKTLIYYATSLADGVPSRFSGSGSGQDYSLTISSLESD

GKAPKTLIYYATSLADGVPSRFSGSGSGQDYSLTISSLESD

GKAPKTLIYYATSLADGVPSRFSGSGSGQDYSLTISSLESD

DTATYYCLQHGESPFT F GSGTKLEIK R A   EP0807125 B1,

DTATYYCLQHGESPFT L GSGTKLEIK - -   Translated Nucleotide sequence from Genomic DNA DTATYYCLQHGESPFT L GSGTKLEIK - -   Amino acid sequence

Figure 7C

SEQUENCE LISTING

<160> NUMBER OF SEQ ID NOS: 5

<210> SEQ ID NO 1
<211> LENGTH: 119
<212> TYPE: PRT
<213> ORGANISM: Artificial Sequence
<220> FEATURE:
<223> OTHER INFORMATION: Synthetic Construct

<400> SEQUENCE: 1

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Lys Phe Ser Arg Tyr
            20                  25                  30

Ala Met Ser Trp Val Arg Gln Ala Pro Gly Lys Arg Leu Glu Trp Val
        35                  40                  45

Ala Thr Ile Ser Ser Gly Gly Ser Tyr Ile Tyr Tyr Pro Asp Ser Val
    50                  55                  60

Lys Gly Arg Phe Thr Ile Ser Arg Asp Asn Val Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Arg Asp Tyr Asp Leu Asp Tyr Phe Asp Ser Trp Gly Gln Gly
            100                 105                 110

Thr Leu Val Thr Val Ser Ser
        115

<210> SEQ ID NO 2
<211> LENGTH: 107
<212> TYPE: PRT
<213> ORGANISM: Artificial Sequence
<220> FEATURE:
<223> OTHER INFORMATION: Synthetic Construct

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Ile Arg Ser Tyr
            20                  25                  30

Leu Thr Trp Tyr Gln Gln Lys Pro Gly Lys Ala Pro Lys Thr Leu Ile
        35                  40                  45

Tyr Tyr Ala Thr Ser Leu Ala Asp Gly Val Pro Ser Arg Phe Ser Gly
    50                  55                  60

Ser Gly Ser Gly Gln Asp Tyr Ser Leu Thr Ile Ser Ser Leu Glu Ser
65                  70                  75                  80

Asp Asp Thr Ala Thr Tyr Tyr Cys Leu Gln His Gly Glu Ser Pro Phe
                85                  90                  95

Thr Leu Gly Ser Gly Thr Lys Leu Glu Ile Lys
            100                 105

<210> SEQ ID NO 3
<211> LENGTH: 357
<212> TYPE: DNA
<213> ORGANISM: Artificial Sequence
<220> FEATURE:
<223> OTHER INFORMATION: Synthetic construct
<220> FEATURE:
<221> NAME/KEY: exon
<222> LOCATION: (1)..(357)

<400> SEQUENCE: 3

```
gaa gtg cag ctg gtg gag tct ggg gga ggc tta gtg aag cct gga ggg    48
Glu Val Gln Leu Val Glu Ser Gly Gly Gly Leu Val Lys Pro Gly Gly
1               5                   10                  15 tcc ctg aaa ctc tcc tgt gca gcc tct gga ttc aag ttt agt aga tat    96
Ser Leu Lys Leu Ser Cys Ala Ala Ser Gly Phe Lys Phe Ser Arg Tyr
            20                  25                  30 gcc atg tct tgg gtt cgc cag gct ccg ggg aag agg ctg gag tgg gtc   144
Ala Met Ser Trp Val Arg Gln Ala Pro Gly Lys Arg Leu Glu Trp Val
        35                  40                  45 gca acc att agt agt ggt ggt agt tac atc tac tat cca gac agt gtg   192
Ala Thr Ile Ser Ser Gly Gly Ser Tyr Ile Tyr Tyr Pro Asp Ser Val
    50                  55                  60 aag ggt cga ttc acc atc tcc aga gac aat gtc aag aac acc ctg tat   240
Lys Gly Arg Phe Thr Ile Ser Arg Asp Asn Val Lys Asn Thr Leu Tyr
65                  70                  75                  80 ctg caa atg agc agt ctg agg tct gag gac acg gcc atg tat tac tgt   288
Leu Gln Met Ser Ser Leu Arg Ser Glu Asp Thr Ala Met Tyr Tyr Cys
                85                  90                  95 gca aga cga gat tac gac ctg gac tac ttt gac tcc tgg ggc caa ggc   336
Ala Arg Arg Asp Tyr Asp Leu Asp Tyr Phe Asp Ser Trp Gly Gln Gly
            100                 105                 110 acc ctt gtc acc gtc tcc tca                                        357
Thr Leu Val Thr Val Ser Ser
        115

<210> SEQ ID NO 4
<211> LENGTH: 318
<212> TYPE: DNA
<213> ORGANISM: Artificial Sequence
<220> FEATURE:
<223> OTHER INFORMATION: Synthetic Construct
<220> FEATURE:
<221> NAME/KEY: exon
<222> LOCATION: (1)..(318)

<400> SEQUENCE: 4 gac atc cag atg acc cag tct cca tcc tcc ctg tct gca tcg gtg gga    48
Asp Ile Gln Met Thr Gln Ser Pro Ser Ser Leu Ser Ala Ser Val Gly
1               5                   10                  15 gac aga gtc act atc act tgc aag gcg agt cgg gac att aga agc tat    96
Asp Arg Val Thr Ile Thr Cys Lys Ala Ser Arg Asp Ile Arg Ser Tyr
            20                  25                  30 tta acc tgg tac cag cag aaa cca ggg aaa gct cct aag acc ctg atc   144
Leu Thr Trp Tyr Gln Gln Lys Pro Gly Lys Ala Pro Lys Thr Leu Ile
        35                  40                  45 tat tat gca aca agc ttg gca gat ggg gtc ccg tcg aga ttc agt ggc   192
Tyr Tyr Ala Thr Ser Leu Ala Asp Gly Val Pro Ser Arg Phe Ser Gly
    50                  55                  60 agt gga tct ggg caa gat tat tct ctc acc atc agc agc ctg gag tct   240
Ser Gly Ser Gly Gln Asp Tyr Ser Leu Thr Ile Ser Ser Leu Glu Ser
65                  70                  75                  80 gac gat aca gca act tac tac tgt cta caa cat ggt gag agt cca acg   288
Asp Asp Thr Ala Thr Tyr Tyr Cys Leu Gln His Gly Glu Ser Pro Thr
                85                  90                  95 ctc ggc tcg ggg acc aag ctg gaa atc aaa                           318
Leu Gly Ser Gly Thr Lys Leu Glu Ile Lys
            100                 105

<210> SEQ ID NO 5
<211> LENGTH: 109
<212> TYPE: PRT
<213> ORGANISM: Artificial Sequence
```

```
<220> FEATURE:
<223> OTHER INFORMATION: Synthetic Construct

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Ile Arg Ser Tyr
                20                  25                  30

Leu Thr Trp Tyr Gln Gln Lys Pro Gly Lys Ala Pro Lys Thr Leu Ile
            35                  40                  45

Tyr Tyr Ala Thr Ser Leu Ala Asp Gly Val Pro Ser Arg Phe Ser Gly
        50                  55                  60

Ser Gly Ser Gly Gln Asp Tyr Ser Leu Thr Ile Ser Ser Leu Glu Ser
65                  70                  75                  80

Asp Asp Thr Ala Thr Tyr Tyr Cys Leu Gln His Gly Glu Ser Pro Phe
                85                  90                  95

Thr Phe Gly Ser Gly Thr Lys Leu Glu Ile Lys Arg Ala
                100                 105
```

MONOCLONAL ANTIBODY AND A METHOD OF USE FOR THE TREATMENT OF LUPUS

CROSS REFERENCE TO RELATED APPLICATIONS

This application is a U.S. national phase application of International PCT Patent Application No. PCT/IB2017/056428, which was filed on Oct. 17, 2017, which claims priority to Indian Application No. 201641036145, which was filed on Oct. 21, 2016. These applications are incorporated by reference herein in their entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is EQIL 008_01US_ST25.TXT. The text file is 7 KB, created on Apr. 18, 2019, and is being submitted electronically via EFS-Web.

FIELD OF THE INVENTION

The present invention relates to a humanized IgG 1 isotype anti-CD6 monoclonal antibody (T1h) that binds to the Scavenger receptor cysteine-rich (SRCR) domain 1 (D1) of CD6 present on the surface of thymic epithelial cells, monocytes, activated T-cells and a variety of other cells types. The invention further relates to methods of inhibiting proliferation of T-cells without blocking the interaction of CD6 with the CD6 ligand Activated Leukocyte Cell Adhesion Molecule (ALCAM). It also relates to compositions and methods useful for the treatment of lupus using the anti-CD6 monoclonal antibody that binds to the SRCR domain 1 (D1) of CD6.

BACKGROUND OF THE INVENTION

Lupus, a prototype of human systemic autoimmune disease, is characterized by a wide variety of multi-organ injuries. It is an autoimmune disease involving antibodies that attack connective tissue. The disease is estimated to affect nearly 1 million Americans, primarily women between the ages of 20-40. The principal form of lupus is a systemic one (systemic lupus erythematosus; SLE) and is associated with the production of antinuclear antibodies, circulating immune complexes, and activation of the complement system. While the pathogenesis of SLE is still not well understood, it is known that B cells, T-cells and monocytes are implicated in playing a critical role in the progression of the disease. Specifically, there is a marked increase in polyclonal B-cell and T-cell activity and such increase can be characterized by the development of T-cells and antibody responses against a variety of self antigens. It is theorized that the activation of T-cells stimulates the production of auto reactive B-cells to a specific epitope and then can spread to other epitopes. Such antibody response may include, as stated above, the production of autoantibodies against self antigens such as anti-nuclear antibodies (ANA) and anti-double stranded DNA antibodies.

SLE can be treated by modulating the immune response by either antagonism of a detrimental process/pathway or stimulation of a beneficial process/pathway. Using neutralizing antibodies that inhibit molecules having immune stimulatory activity or directly inhibiting the immune response are effective ways to ameliorate immune related diseases.

CD6 is an important cell surface protein predominantly expressed by human T-cells and a subset of B-cells, as well as by some B-cell chronic lymphocytic leukemias and neurons. CD6 is a member of a large family of proteins characterized by having at least one domain homologous to the scavenger receptor cysteine-rich domain (SRCR) of type I macrophages. Blocking studies using anti-CD6 monoclonal antibodies (mAbs) suggest that CD6 plays an important role in T-cell development by regulating T-cell adhesive interactions with thymic epithelial (TE) cells.

Additional studies have shown that CD6 can function as an important accessory molecule in T-cell activation. For example, certain anti-CD6 mAb are directly mitogenic for T-cells [1, 2], whereas others are able to co-stimulate T-cell proliferation in conjunction with anti-CD3, anti-CD2 or phorbol 12 myristate 13 acetate (PMA) [1, 3, 4]. Yet additional evidence of the role of CD6 in T-cell activation comes from studies showing that CD6 becomes hyperphosphorylated on Ser and Thr residues [5, 6, 7] and phosphorylated on Tyr residues [8] following T-cell activation. These and other studies implicate CD6 as an important modulator of both immature and mature T-cell function in vivo, affecting both T-cell activation and signal transduction.

The extracellular domain of the mature CD6 protein is composed of three SRCR domains (hereinafter designated D1, D2, and D3). D3 corresponding to the membrane proximal SRCR domain followed by a short 33-amino-acid stalk region. These extracellular domains are anchored to the cell membrane via a short transmembrane domain followed by a cytoplasmic domain of variable length [19].

Studies using CD6-immunoglobulin fusion proteins, containing selected extracellular domains of CD6 fused to human $IgG_1$ constant domains (CD6-Rgs), led to the identification and cloning of a CD6 ligand, designated "activated leukocyte cell adhesion molecule" (ALCAM) [11, 12]. ALCAM binds to domain 3 of CD6 corresponding to the membrane proximal SRCR domain [13].

Studies of the role of CD6/ALCAM interactions in T-cell regulation have shown that this receptor-ligand pair is able to mediate the adhesion of CD6 expressing cells to thymic epithelial cells [12]. This and other evidence suggests that CD6/ALCAM interactions are important for modulating T-cell development and activation.

Although the functional characterization of CD6 remains incomplete, an anti-CD6 mAb has been successfully applied in a clinical setting to purge bone marrow of T-cells and T-cell precursors. These findings further support the hypothesis that CD6 plays an important role in modulating T-cell function in vivo. CD6 is also reported to be part of the immunologic synapse mediating early and late T-cell-antigen presenting cells (APC) interaction.[14]

U.S. Pat. No. 6,372,215 discloses antibodies and other binding agents that bind specifically to SRCR domains 3 (D3) of human CD6 (hCD6) or human CD6 stalk domain (CD6S) and inhibit activated leukocyte cell adhesion molecule (ALCAM) binding to CD6.

Earlier publications and patents disclosed sequences of the murine anti-CD6 (IOR-T1) monoclonal antibody and the amino acid modifications that were carried out to humanize IOR-T1 to T1h (humanized IOR-T1). U.S. Pat. No. 5,712,120 and its equivalent EP 0699755 disclose specific methods to humanize murine monoclonal antibodies and the sequence of IOR-T1 and T1h. U.S. Pat. No. 6,572,857 and its equivalent EP 0807125 disclose the sequence of IOR-T1 and T1h (humanized IOR-T1). The Roque-Navarro publication [15] discusses specific methods to humanize murine monoclonal antibodies and the sequence of IOR-T1 and T1h. PCT/IN2008/00562 entitled 'A Monoclonal Antibody and a Method Thereof_ discusses the targeting of CD6 as a treatment of an autoimmune disease such as multiple sclerosis, transplant rejection and graft-versus-host diseases.

There is an urgent need for improved therapeutic methods and compositions for treatment of lupus. At present, lupus is typically treated with corticosteroids and immunosuppressants. In some embodiments, antibodies are used that significantly deplete lymphocytes and in other embodiments the lymphocytes are not depleted. It would be advantageous to provide an anti-CD6 monoclonal antibody that inhibits T-cell activation by binding to CD6, the D1 domain, without interfering with the binding of ALCAM to CD6 and wherein the anti-CD6 monoclonal antibody has the ability to treat lupus and inhibit proliferation of T-cells that usually occurs in a lupus type disease.

SUMMARY OF THE INVENTION

The present invention relates to an anti-CD6 monoclonal antibody (T1h) that reduces or prevents the activation of T-cells, inhibits T-cell proliferation, reduces induction of complement-dependent cytotoxicity (CDC) and binds to domain 1 (D1) of CD6 without interfering with ALCAM binding to CD6 and wherein the anti-CD6 monoclonal antibody comprises amino acid sequences of SEQ ID NO: 1 and SEQ ID NO: 2 or sequences having at least about 97% identity thereto.

In one aspect the present invention provides for a method of treating lupus, the method comprising administering to a subject suffering from the effects of lupus a therapeutically effective amount of an anti-CD6 monoclonal antibody comprising or consisting of amino acid sequences of SEQ ID NO: 1 and SEQ ID NO: 2.

The methods of this invention can be used to treat a subject who has one or more manifestations or systems of lupus, including, without limitation, systemic lupus erythematosus, lupus nephritis, cutaneous lupus erythematosus, central nervous system (CNS) lupus, cardiovascular manifestations, pulmonary manifestations, hepatic manifestations, haematologieal manifestations, gastrointestinal manifestations, musculoskeletal manifestations, neonatal lupus erythematosus, childhood systemic lupus erythematosus, drug-induced lupus erythematosus, anti-phospholipid syndrome, or complement deficiency syndromes resulting in lupus manifestations.

In another aspect, the present invention provides for a polynucleotide encoding an anti-CD6 monoclonal antibody comprising amino acid sequences of SEQ ID NO: 1 and SE Q ID NO: 2, a vector including the polynucleotides encoding the amino acid sequences, and a host cell including the vector. The cell may be eukaryotic (e.g., mammalian such a human, mouse, monkey or rabbit cell) or may be prokaryotic (e.g., a bacterial cell such as an E. coli cell).

In yet another aspect, the present invention provides for a method of treating lupus in a subject, the method comprising administering to the subject an anti-CD6 monoclonal antibody comprising amino acid sequences of SEQ ID NO: 1 and SEQ ID NO: 2 or antigen-binding fragment thereof, wherein the use of the anti-CD6 monoclonal antibody shows a reduction in pro inflammatory cytokines.

Another aspect of the present invention provides for a method for modulating inflammatory conditions using an anti-CD6 monoclonal antibody comprising amino acid sequences of SEQ ID NO: 1 and SEQ ID NO: 2. The monoclonal antibody may be combined with is a chemotherapeutic agent, an immunosuppressive agent, an anti-malarial drug, a cytotoxic agent, an integrin antagonist, a cytokine antagonist, or a hormone.

The immunosuppressant may include prednisone, methotrexate, azathioprine or cyclophosphamide. Importantly, the administration of the anti-CD6 monoclonal antibody of the present provides for a reduced amount of immunosuppressant thereby avoiding the negative effects of immunosuppressants that can weaken the body's defense against other potential pathogens, thereby making the subject extremely susceptible to infection and other potentially fatal diseases, such as cancer.

In another aspect, the present invention also provides for a method to reduce activation of T-cells in a subject with an elevated level of anti-nuclear antibodies (ANA) and/or anti-double-stranded DNA (dsDNA) antibodies, comprising administering to the patient a therapeutically effective amount of the anti-CD6 monoclonal antibody of the present invention.

In yet a further aspect, the present invention also provides methods of treating a lupus patient in need thereof, comprising administering to the patient a therapeutically effective amount of an anti-CD6 antibody in combination with at least a second compound. The second compound is typically a therapeutic agent that is used to treat lupus, for example, a standard-of-care or experimental treatment. In the combination therapy methods of this invention, the anti-CD6 antibody and the additional therapeutic agent can be administered in any order as appropriate for the patient. The anti-CD6 antibody and the additional agent(s) can be administered concurrently or sequentially. For example, the additional agent(s) can be administered before or after the anti-CD6 therapy. Also provided in this invention are kits useful for such combination therapy.

Another aspect of the present invention provides for a monoclonal antibody which specifically binds to Scavenger receptor cysteine-rich (SRCR) domain 1 (D1) of CD6 which comprises heavy chain and light chain encoded by the nucleotide sequence set forth in SEQ ID NO: 3 or a complement thereof; and (b) a nucleic acid molecule comprising the nucleotide sequence set forth in SEQ ID NO: 4 or a complement thereof.

Yet another aspect of the present invention provides for the use of the anti-CD6 antibody described above in the manufacture of medicament useful for the treatment of lupus.

Another aspect of the present invention provides for a treatment method to a subject who does not have an autoimmune disease other than lupus.

In a further aspect, the present invention provides for an article of manufacture comprising: (a) a container comprising the anti-CD6 monoclonal antibody of the present invention; and (b) a package insert with instructions for treating lupus in a subject, wherein the instructions indicate that an amount of the antibody is administered to the subject that is effective to provide reduce the negative effects of lupus.

The foregoing and other objects and aspects of the present invention are explained in detail in the drawings herein and the specification set forth below.

BRIEF DESCRIPTION OF THE FIGURES

FIG. 7(A) Nucleotide sequence of VH (SEQ ID NO: 3) and Vk (SEQ ID NO: 4) of T1h derived from plasmid and genomic DNA; (B) Amino acid sequence of VH (SEQ ID NO: 1) and Vk (SEQ ID NO: 2); (C) Comparison of Vk amino acid sequence disclosed in previous publications (SEQ ID NO: 5) as compared to the sequence disclosed in this patent (SEQ ID NO: 2) to highlight the sequence differences.

DETAILED DESCRIPTION OF THE INVENTION

Figure 1:
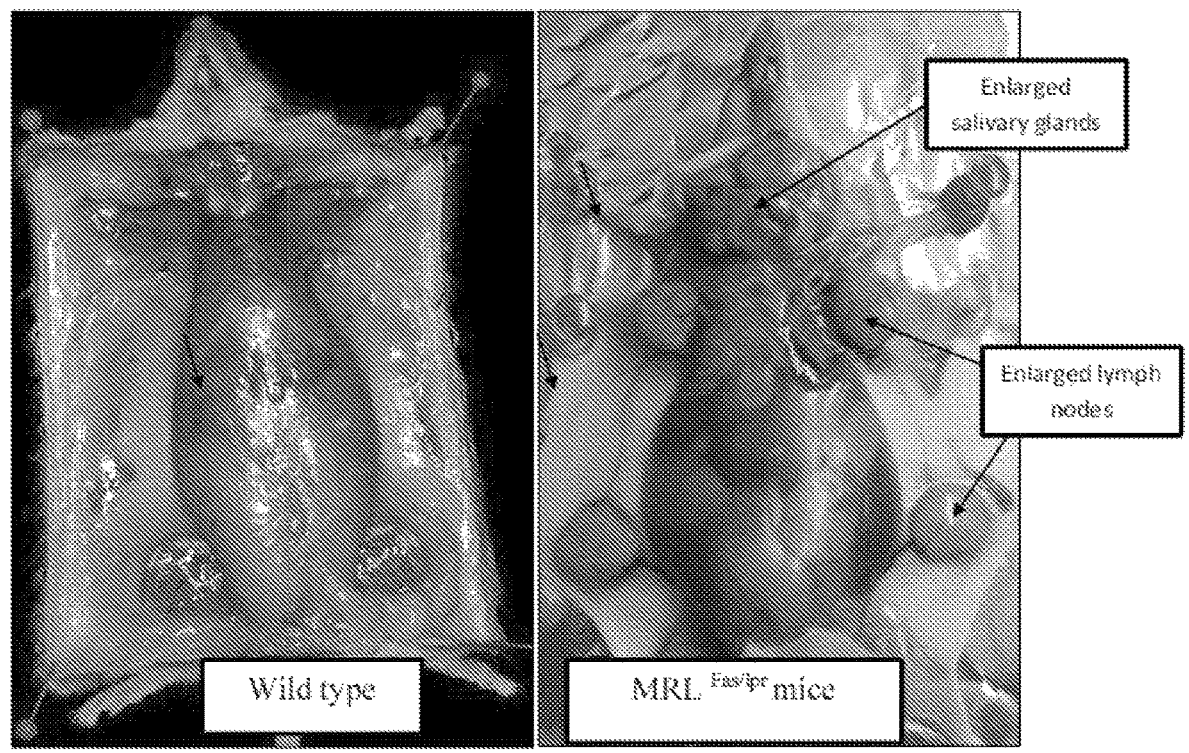
FIG. 1 shows the external examination of lymph nodes of normal and SLE mouse: SLE mice (right panel) shows swollen lymph nodes (marked with arrows) and enlarged salivary glands

The present invention provides for an anti-CD6 monoclonal antibody capable of binding to domain 1 (D1) of CD6 and inhibits T-cell proliferation without interfering with ALCAM binding, and wherein the anti CD6 monoclonal antibody reduces inflammatory conditions due to systemic lupus. Further it has been found that the anti-CD6 monoclonal antibody does not induce complement dependent cytotoxicity (CDC) in vitro.

The practice of the present invention will employ, unless otherwise indicated, conventional techniques of immunology, molecular biology, microbiology, cell biology and recombinant DNA, which are within the skill of the art. See, e.g., Sambrook, et al. MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds.

(1995)), Harlow and Lane, eds. (1988) ANTIBODIES, A LABORATORY MANUAL, and ANIMAL CELL CULTURE (R. I. Freshney, ed. (1987)).

Definitions

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular.

In describing and claiming the present invention, the following terminology will be used in accordance with the definitions set out herein.

As used herein, "Lupus" is an autoimmune disease or disorder involving antibodies that attack connective tissue. The principal form of lupus is a systemic one, systemic lupus erythematosus (SLE), including cutaneous SLE and subacute cutaneous SLE, as well as other types of lupus (including nephritis, exfrarenal, cerebritis, pediatric, non-renal, discoid, and alopecia).

As used herein, "Anti-CD6 antibody" is generally an antibody that bind specifically to SRCR domain 1 (D1) of human CD6 (hCD6). In preferred aspects of the invention, antibodies and other immunoglobulins, including native and artificially modified antibodies and antibody fragments, are provided that bind specifically to human SRCR domain 1 of CD6 and that do not interfere with the activated leukocyte cell adhesion molecule (ALCAM) binding to CD6.

As used herein, a "subject" is a human subject. Generally, such subject is eligible for treatment for lupus. For the purposes herein, such eligible subject is one that is experiencing or has experienced one or more signs, symptoms, or other indicators of lupus or has been diagnosed with lupus, whether, for example, newly diagnosed, previously diagnosed with a new flare, or chronically steroid dependent with a new flare, or is at risk for developing lupus.

As used herein, 'symptoms_ or other indicators used to diagnose lupus may include rashes on the cheeks, discoid rash, or red raised patches; photosensitivity, such as reaction to sunlight; oral ulcers, such as ulcers in the nose or mouth; arthritis, such as non-erosive arthritis involving two or more peripheral joints; renal disorder, such as excessive protein in the urine; neurologic signs, such as seizures (convulsions); and hematologic symptoms, such as hemolytic anemia, leukopenia, lymphopenia or thrombocytopenia.

As used herein, 'monoclonal antibody_ (mAb) refers to an antibody of a population of substantially homogeneous antibodies; that is, the individual antibodies in that population are identical except for naturally occurring mutations that may be present in minor amounts. Monoclonal antibodies are highly specific, being directed against a single antigenic determinant, an 'epitope._ Therefore, the modifier 'monoclonal_ is indicative of a substantially homogeneous population of antibodies directed to the identical epitope and is not to be construed as requiring production of the antibody by any particular method. It should be understood that monoclonal antibodies can be made by any technique or methodology known in the art; including e.g., recombinant DNA methods known in the art, or methods of isolation of monoclonal recombinantly produced using phage antibody libraries.

As used herein, "Complement-dependent cytotoxicity" or "CDC" refers to the ability of a molecule to lyse a target in the presence of complement. The complement activation pathway is initiated by the binding of the first component of the complement system to a molecule (e.g. an antibody) complexed with a cognate antigen.

As used herein, "cytokine" is a generic term for proteins released by one cell population that act on another cell as intercellular mediators. Examples of such cytokines are lymphokines, monokines; interleukins (ILs) such as IL-1, IL-I, IL-2, IL-3, IL-4, IL-5, IL-6, IL-7, IL-8, IL-9, IL-11, IL-12, IL-15; a tumor necrosis factor such as TNF- or TNF-$\oint$.

As used herein, "growth-inhibitory" antibodies are those that prevent or reduce proliferation of a cell expressing an antigen to which the antibody binds. For example, the antibody may prevent or reduce proliferation of T-cells in vitro and/or in vivo.

As used herein, "therapeutically effective amount" refers to an amount effective, at dosages and for periods of time necessary, to achieve a desired therapeutic result.

As used herein, an "autoimmune disease" is a disease or disorder arising from and directed against an individual's own tissues or organs and results from, or is aggravated by, the production by B-cells of antibodies that are reactive with normal body tissues and antigens, such as, secretion of an autoantibody that is specific for an epitope from a self-antigen (e.g. a nuclear antigen).

As used herein, determination of apoptosis (programmed cell death) by specific antibodies, that being, those that "induce or do not induce apoptosis, e.g. of a T-cell, can be determined by standard apoptosis assays, such as binding of annexin V, fragmentation of DNA, cell shrinkage, dilation of endoplasmic reticulum, cell fragmentation, and/or formation of membrane vesicles (called apoptotic bodies).

It is understood that aspects of the present invention described herein also include "consisting of" and "consisting essentially of" aspects.

According to the first aspect of the present invention, there is provided an anti-CD6 monoclonal antibody that is capable of specifically binding to D1 domain of CD6 without interfering with the binding of ALCAM to CD6 comprising SEQ ID NO: 1 and SEQ ID NO: 2. The nucleotide sequences encoding the anti-CD6 monoclonal antibody includes SEQ ID NO: 3 and SEQ ID NO: 4, respectively or nucleotide sequences have at least 90% identity thereto and encode for SEQ ID NO: 1 and SEQ ID NO: 2.

Methods for Producing the Anti-CD6 Monoclonal Antibodies of the Invention

The present invention further provides methods for producing the disclosed anti-CD6 antibodies. These methods encompass culturing a host cell containing isolated nucleic acid(s) encoding the antibodies of the invention. As will be appreciated by those in the art, this can be done in a variety of ways, depending on the nature of the antibody.

In general, nucleic acids are provided that encode the antibodies of the invention. The polynucleotides can be in the form of RNA or DNA. Polynucleotides in the form of DNA, cDNA, genomic DNA, nucleic acid analogs, and synthetic DNA are within the scope of the present invention. The DNA may be double-stranded or single-stranded, and if single stranded, may be the coding (sense) strand or non-coding (anti-sense) strand. The coding sequence that encodes the an anti-CD6 monoclonal antibody may be identical to the coding sequence provided herein or may be a different coding sequence, which sequence, as a result of the redundancy or degeneracy of the genetic code, encodes the same polypeptides as the DNA provided herein.

In some embodiments, nucleic acid(s) encoding the anti-CD6 monoclonal antibody of the present invention are incorporated into expression vectors, which can be extrachromosomal or designed to integrate into the genome of the host cell into which it is introduced. Expression vectors can contain any number of appropriate regulatory sequences (including, but not limited to, transcriptional and translational control sequences, promoters, ribosomal binding sites, enhancers, origins of replication, etc.) or other components (selection genes, etc.), all of which are operably linked as is well known in the art. In some cases two nucleic acids are used and each put into a different expression vector (e.g. heavy chain in a first expression vector, light chain in a second expression vector), or alternatively they can be put in the same expression vector. It will be appreciated by those skilled in the art that the design of the expression vector(s), including the selection of regulatory sequences may depend on such factors as the choice of the host cell, the level of expression of protein desired, etc.

In general, the nucleic acids and/or expression can be introduced into a suitable host cell to create a recombinant host cell using any method appropriate to the host cell selected (e.g., transformation, transfection, electroporation, infection), such that the nucleic acid molecule(s) are operably linked to one or more expression control elements (e.g., in a vector, in a construct created by processes in the cell, integrated into the host cell genome). The resulting recombinant host cell can be maintained under conditions suitable for expression (e.g. in the presence of an inducer, in a suitable non-human animal, in suitable culture media supplemented with appropriate salts, growth factors, antibiotics, nutritional supplements, etc.), whereby the encoded polypeptide(s) are produced. In some cases, the heavy chains are produced in one cell and the light chain in another.

The expression vectors can be transfected into host cells such as *E. coli* cells, simian COS cells, Chinese Hamster Ovary (CHO) cells, or myeloma cells that do not otherwise produce immunoglobulin protein, to obtain the synthesis of monoclonal antibodies in the recombinant host cells. Y east, insect, and plant cells can also be used to express recombinant antibodies. In some embodiments, the antibodies can be produced in transgenic animals such as cows or chickens.

General methods for antibody molecular biology, expression, purification, and screening are described, for example, in Antibody Engineering, edited by Kontermann & Dubel, Springer, Heidelberg, 2001 and 2010.

Mode of Administration

For administration in the methods of use described below, the anti-CD6 monoclonal antibody may be mixed, prior to administration, with a non-toxic, pharmaceutically acceptable carrier substance (e.g. normal saline or phosphate-buffered saline), and will be administered using any medically appropriate procedure, e.g., parenteral administration (e.g., injection) such as by intravenous or intra-arterial injection.

Formulations of the anti-CD6 monoclonal antibody used in accordance with the present invention may be prepared by mixing an antibody having the desired degree of purity with optional pharmaceutically acceptable carriers, excipients or stabilizers in either the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives such as octadecyl di methyl benzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol and m-cresol; low molecular weight (less than about 10 residues) polypeptides; proteins, such as serum albumin, gelatin, or immunoglobulins; hydrophilic polymers such as polyvinyl pyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEENú, PLURONICSú or polyethylene glycol (PEG).

The anti-CD6 monoclonal antibody may also be entrapped in microcapsules prepared, for example, by coacervation techniques or by interfacial polymerization, for example, hydroxymethyl cellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are well known in the art.

Sustained-release preparations may be prepared. Suitable examples of sustained-release preparations include semipermeable matrices of solid hydrophobic polymers containing the anti-CD6 monoclonal antibody, which matrices are in the form of shaped articles, e.g. films, or microcapsules. Examples of sustained-release matrices include polyesters, hydrogels, copolymers of L-glutamic acid, non-degradable ethylene-vinyl acetate and degradable lactic acid-glycolic acid copolymers.

The anti-CD6 monoclonal antibody may be administered to a subject, in accord with known methods, such as intravenous administration as a bolus or by continuous infusion over a period of time, by intramuscular, intraperitoneal, intracerobrospinal, subcutaneous, intra-articular, intrasynovial, intrathecal or oral routes. Intravenous or subcutaneous administration of the anti-CD6 monoclonal antibody is preferred.

Treatment of lupus related diseases according to the present invention includes a "therapeutically effective amount" of the anti-CD6 monoclonal antibody used. Notably, a therapeutically effective amount may vary according to factors such as the disease state, age, sex, and weight of the individual, and the ability of the anti-CD6 monoclonal antibody to elicit a desired response in the individual.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. The efficient dosages and the dosage regimens for the anti-CD6 monoclonal antibodies used in the present invention depend on the severity of the lupus-type disease and may be determined by the persons skilled in the art.

An exemplary, non-limiting range for a therapeutically effective amount of the anti-CD6 monoclonal antibody used in the present invention is about 0.01-100 mg/kg per subject body weight, such as about 0.01-50 mg/kg, for example about 0.01-25 mg/kg. A medical professional having ordinary skill in the art may readily determine and prescribe the effective amount of the pharmaceutical composition required. For example, a physician could start doses of the anti-CD6 monoclonal antibody at levels lower than that required in order to achieve the desired therapeutic effect and gradually increase the dosage until the desired effect is achieved.

In one embodiment, the anti-CD6 monoclonal antibody is administered by infusion in a weekly dosage of from 1 to 500 mg/kg per subject body weight, such as, from 20 to 200 mg/kg. Such administration may be repeated, e.g., 1 to 8 times, such as 3 to 5 times. In the alternative, the administration may be performed by continuous infusion over a period of from 2 to 24 hours, such as, from 2 to 12 hours.

In one embodiment the anti-CD6 monoclonal antibody is administered in a weekly dosage of from 10 mg to 200 mg, for up to 7 times, such as from 4 to 6 times. The administration may be performed by continuous infusion over a period of from 2 to 24 hours, such as, from 2 to 12 hours. Such regimen may be repeated one or more times as necessary, for example, after 6 months or 12 months.

The Examples which follow are set forth to aid in understanding the invention but are not intended to, and should not be construed to limit its scope in any way. The Examples do not include detailed descriptions for conventional methods employed in the assay procedures. Such methods are well known to those of ordinary skill in the art and are described in numerous publications including by way of examples.

Example 1

CD6 is a co-stimulatory molecule, predominantly expressed on lymphocytes and is associated with many autoimmune disease [16, 17]. The anti-mouse CD6 (-mCD6) binds specifically to domain 1 of CD6 and is a surrogate antibody for Itolizumab. Previous studies using this antibody demonstrated significant amelioration of EAE (Experimental Autoimmune Encephalomyelitis) a model for multiple sclerosis in mice. In the present study, the antibody is evaluated in MRL$^{Fas/lpr}$ mice, a relevant mouse model for lupus like disease in humans. -mCD6 treatment showed significant reduction in lymphadenopathy, spleen and salivary glands weights (p<0.05) compared to isotype control. -mCD6 treated animals showed significant hypo proliferation to anti-CD3 mediated T-cell proliferation assays with concurrent reduction in release of pro inflammatory cytokines like IFN-γ (p<0.04) and TNF- (p<0.09).

MRL$^{Fas/lpr}$ is a well-known animal model used in Lupus like autoimmune diseases [18-21]. This model has spontaneous mutation in Fas gene, predominantly affecting the proliferation of B and T-cells. This mutation prevents apoptosis with uncontrolled proliferation of lymphocytes thereby resulting in massive enlargement of lymph nodes (lymphadenopathy), salivary glands and spleen as shown in FIG. 1. This model also shows glomerulonephritis which resembles Lupus Nephritis in humans [22]. In mice, the disease onset is 8 week onwards till mortality between weeks 16-18 [20, 21].

Systemic Lupus Erythematosus (SLE) is an autoimmune inflammatory disease that affects mostly middle-aged women (ratio 9:1 women to men). Characteristics of SLE include skin eruptions, joint pain, recurrent pleurisy, and kidney disease.

Figure 6:
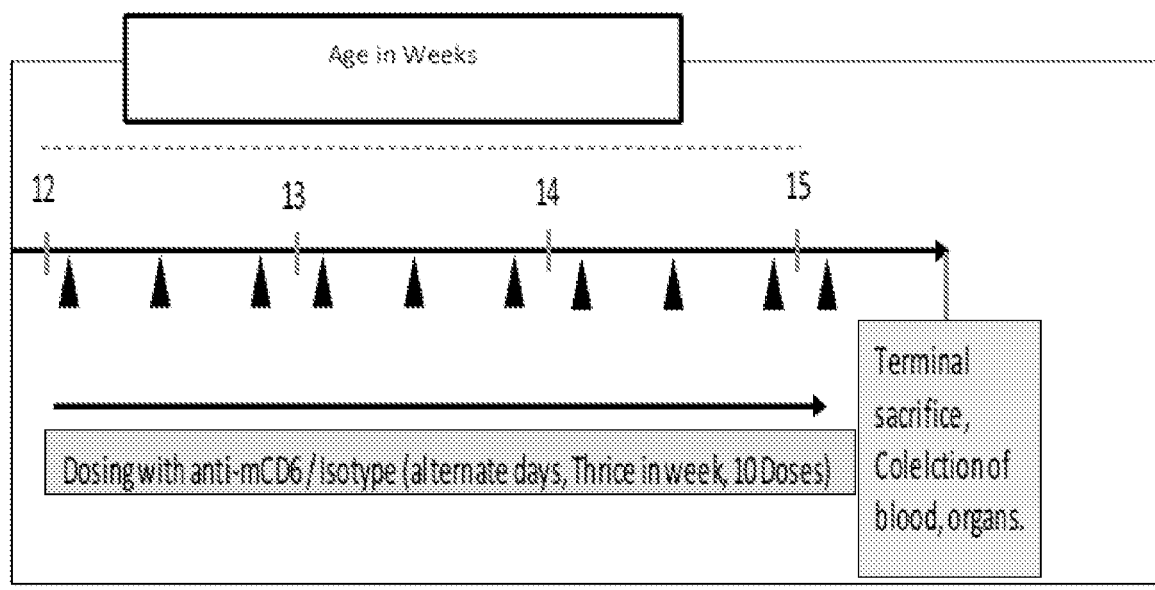
FIG. 6 shows the dosing regimen for treatment of mice.

This study describes the use of -mCD6 in this lupus model. Animals (n=6 per group, age: 12 weeks) were treated with 60 and 600 1 g/dose of -mCD6 or 60 1 g of Rat IgG (Isotype control) intraperitoneally (i.p.) for 10 Days (3 weeks per dose). Animals were sacrificed at the age of 16 weeks. The testing regime is shown in FIG. 6. At the end of study the following parameters were evaluated:

Measurement of lymphadenopathy followed by organ collection and evaluation at the end of the study.
Proteinuria—Measured during the duration of the study.
Blood collection at study terminus.
Proliferation assays with lymph nodes and spleen.
Anti-nuclear antibody and anti-ds DNA antibody measurement from mouse serum.
Cytokine analysis from the proliferation assay.

Results:

Decrease in Lymphadenopathy with Associated Reduction in Certain Lymphoid Organs with -mCD6.

Figure 2:
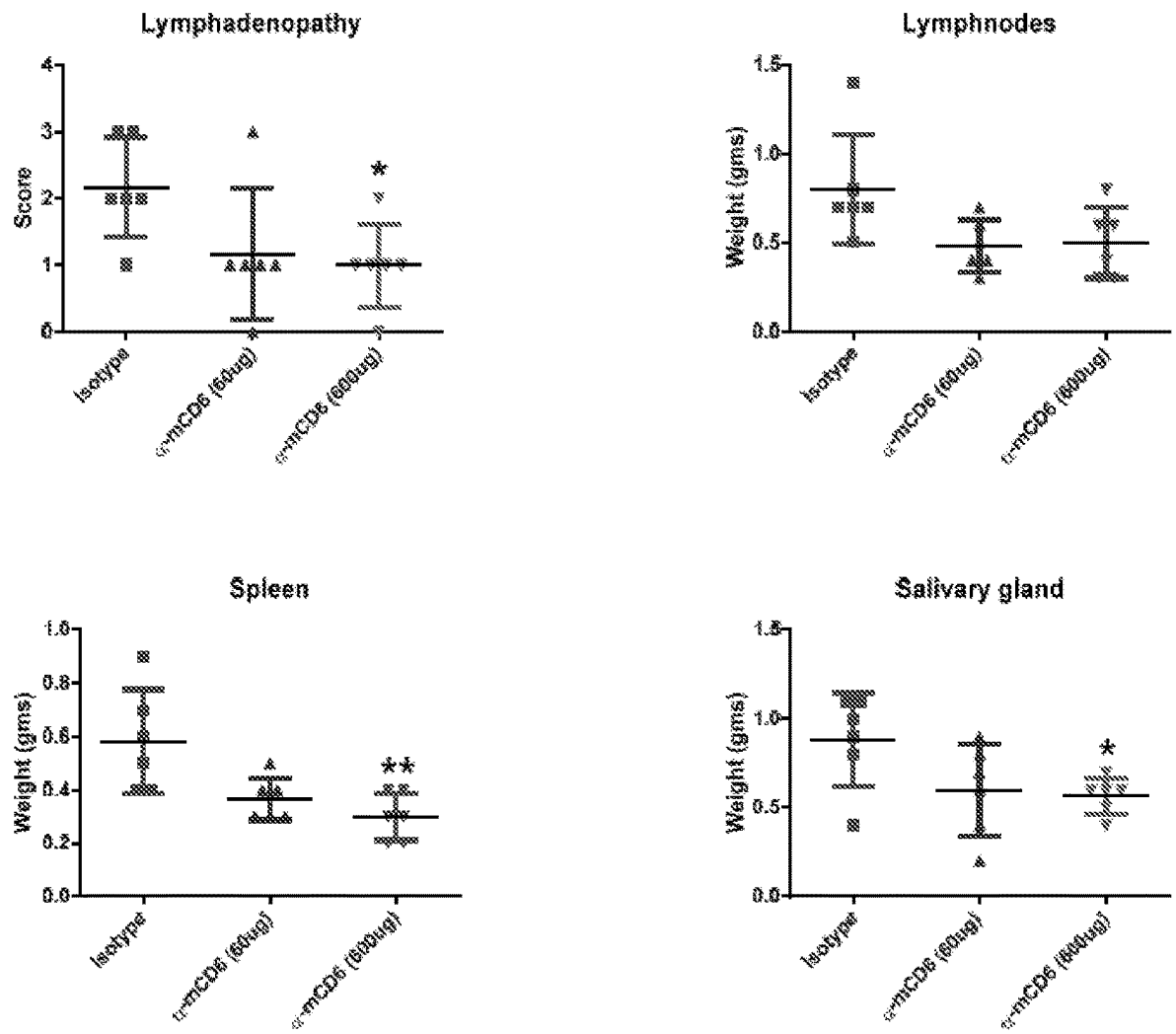
FIG. 2 shows comparison of organ weights and lymphadenopathy: Animals (n=6) were treated with 60 or 600 1 g of -mCD6 or 60 1 g Rat IgG (Isotype control) intraperitoneally (i.p.) for 10 Days (3 weeks per dose, alternate days). At the end of study lymphadenopathy (a) was measured (Scale 0-3; low/no swollen lymph nodes to severe) and organ weights were measured (b-d). Significant reduction observed in lymphadenopathy score (a) and size of spleen (c) and salivary glands (d) (p<0.05, One way A NOVA followed by Multiple comparison test).

Lupus mice treated with -mCD6 antibody showed significant reduction in lymphadenopathy score and weight of the organs i.e., spleen, salivary glands compared to isotype control as shown in FIG. 2. There was no difference in the proteinuria, kidney and thymus size measured between groups (data not shown).

Figure 3:
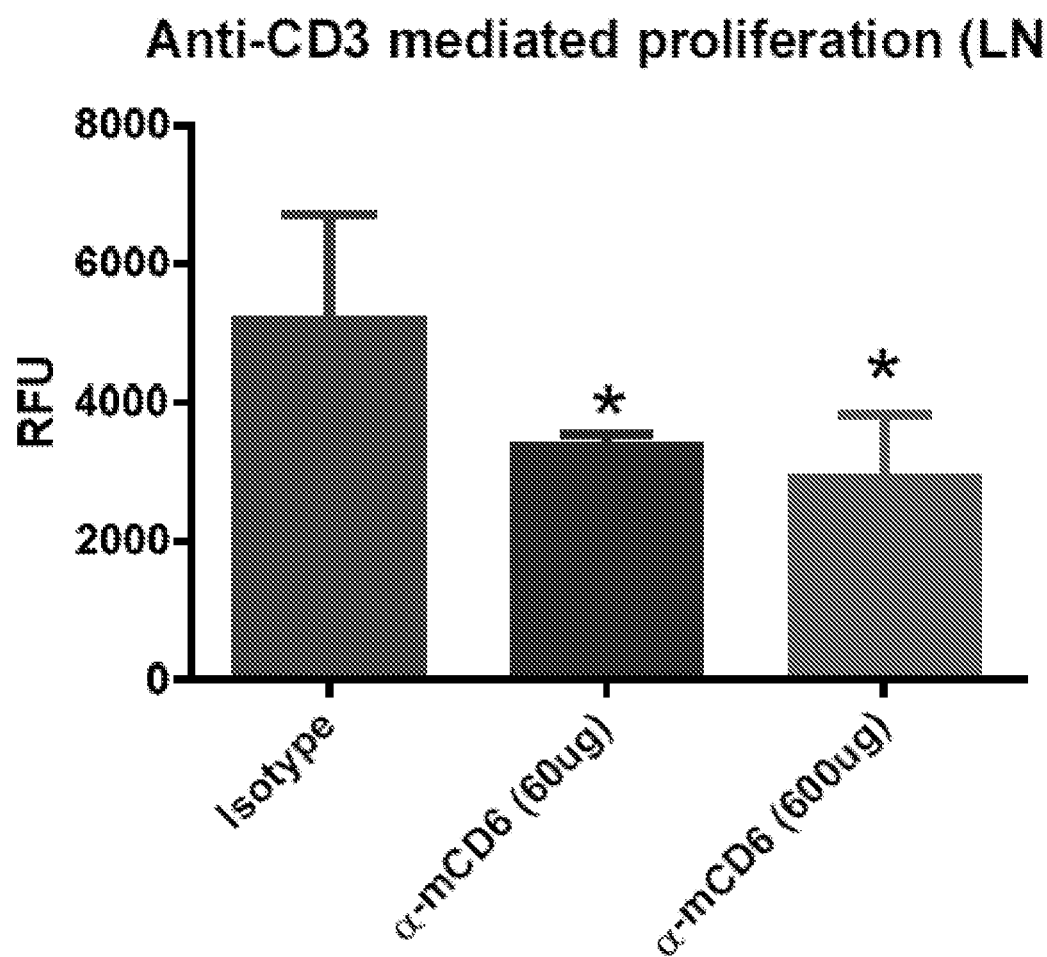
FIG. 3 shows the results of cell proliferation assay: Single cell suspensions of lymphatic cells from each group were subjected to anti-mCD3 mediated proliferation. -mCD6 treated group showed significant (p<0.05; One way ANOVA followed by Multiple comparison test) hypo responsiveness to anti-CD3 mediated proliferation.

-mCD6 Treated Shows Hypo Responsiveness to Anti-CD3 Mediated Proliferation with Associated Reduction in Proinflammatory Cytokines Lymph node derived cells from animals treated with -mCD6 show hypo responsiveness to anti-CD3 mediated proliferation of T-cells (p<0.05) as compared to Isotype treated group, indicating suppression of T-cell activation probably associated with the disease suppression, as shown in FIG. 3.

Figure 4:
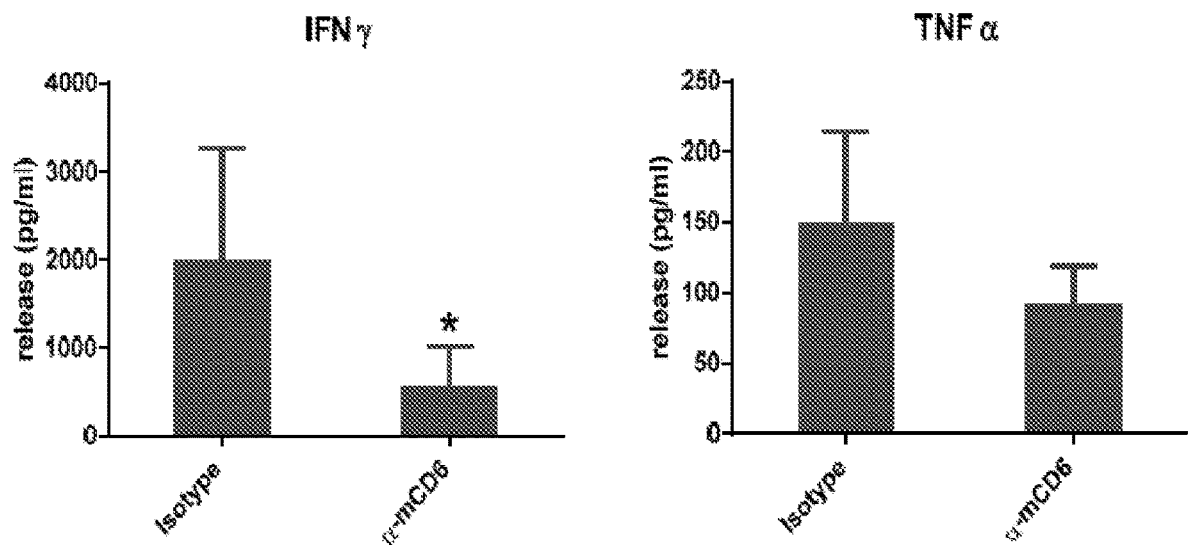
FIG. 4 shows the results of the cytokine analysis: Supernatants from the proliferation assay is used to measure the cytokine release by Cytokine Bead Array (CBA) analysis. -mCD6 showed significant decrease in the release of IFN-∴ (p<0.05; Mann-Whitney test) in the treated group (both the groups were combined for analysis purpose) compared to isotype group. TNF- was also lower in the treated group as compared to Isotype treated group but the difference not statistically significant (p<0.09).

Cytokines play a major role in pathogenesis of SLE [23-26]. Th1/Th2/Th17 cytokines were measured from the supernatants from the proliferation assay. -mCD6 treated groups showed lower release of pro inflammatory cytokines like IFN-γ and TNF- as compared to control group, as shown in FIG. 4. However, there was no difference in the other cytokines (IL-2, IL-6, IL-10 and IL-17) evaluated between the groups.

-mCD6 Treated Animals Possibly Impacts B Cell Response

Figure 5:
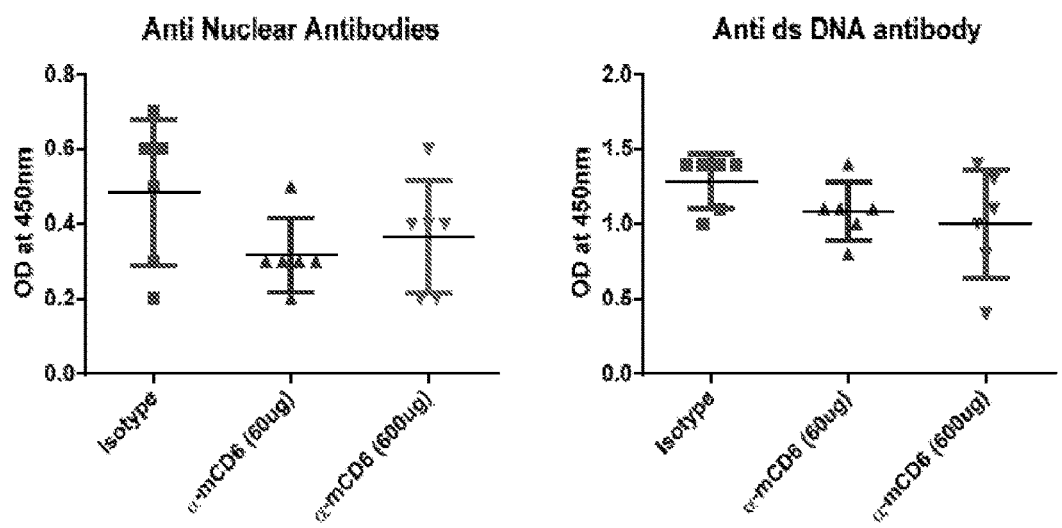
FIG. 5 shows the results of serum ANA and anti-ds DNA antibody analysis: Serum from the isotype and -mCD6 treated mice used to analyse (1:100 dilution) the ANA and anti-ds DNA antibodies using ELISA.

Anti-Nuclear Antibody (ANA) and anti-ds DNA are the key auto antibodies generally observed in Lupus disease. This is also observed in this animal model [18, 20, 21, 27]. Treatment with -mCD6 showed lesser ANA and anti-ds DNA antibodies in the mice serum, as shown in FIG. 5, as compared to isotype treated group. The reduction was not however statistically significant.

In this initial dose finding study both 60 and 600 1 g/dose showed comparable efficacy in the physical and biological endpoints measured. This would suggest a dose saturation by 60 1 g/dose. Thus, it has been shown that use of the -mCD6 antibody is able to alleviate Lupus like symptoms in this mice model.

Example 2

T1h and ALCAM does not Bind to the Same Domain on CD6 by ELISA

When varying concentrations of ALCAM-Fc was incubated along with a fixed concentration of T1h in a CD6-Fc coated ELISA plate, T1h was detected at all concentration of ALCAM-Fc. This experiment suggested that T1h binds to a different domain from the ALCAM binding domain (Domain 3).

Figure 8:
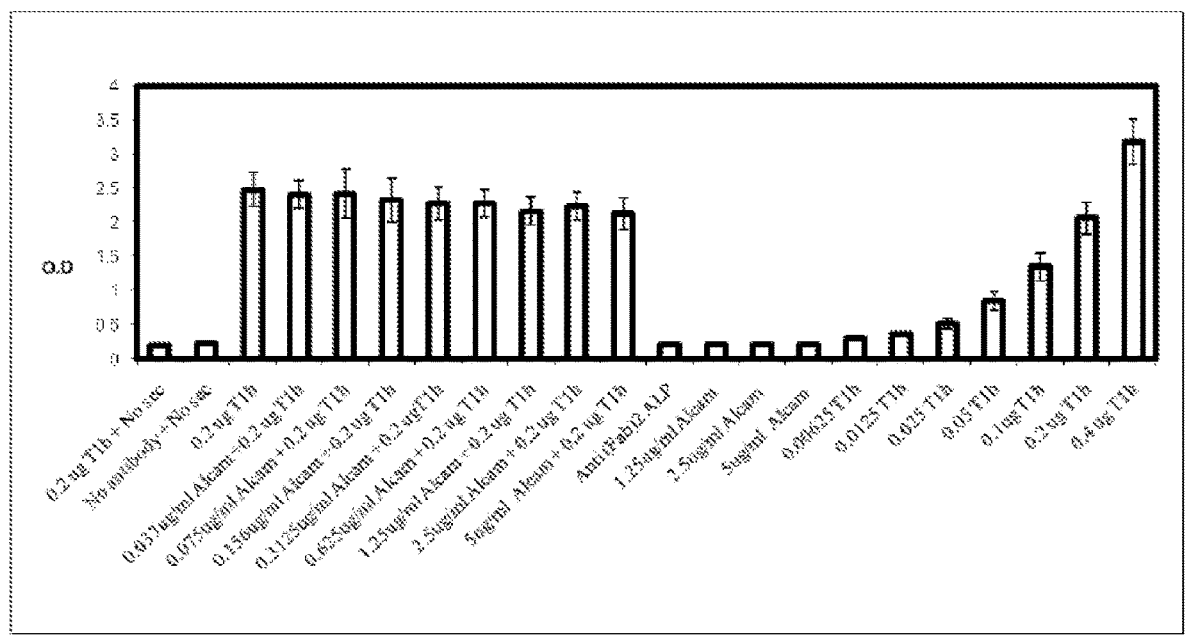
FIG. 8 shows E LISA reading of plate tethered with CD6-Fc in the presence of T1h and ALCAM or T1h alone.

The rhCD6FC/Chimera (R and D systems) (100≈g/ml) was diluted in coating buffer and 100≈l was added to each well of a 96 well Nunc-Maxisorp plate. The plate was then incubated at 4éC overnight. The Plate was washed thrice with PBS Tween 20. Subsequently, 200≈l of blocking solution (2% BSA+0.1% Tween 20 in 1×PBS) was added and incubated for 1 hour at 37éC. After incubation, the plate was washed again with PBS Tween thrice, followed by the addition of T1h monoclonal antibody (0.2 mg/ml) and .rhALCAMFc (R and D systems) at varying concentrations. This was then incubated for an hour at 37éC. The plate was washed 3 times subsequently with PBS Tween. To the wells 200≈l of anti human IgG (Fab)$_2$ ALP (1:20000) diluted in blocking buffer was added and incubated for 1 hour at 37éC. The plate was washed thrice with PBS tween and 200≈l of p-Nitrophenyl Phosphate (PNPP) substrate is added to each well and incubated at 37éC till color develops around 15 minutes. Reading was taken at 405 nm using a BIOTEK Micro Plate Reader. The experiment indicates that the presence of ALCAM in varying concentrations does not prevent T1h from binding to a CD6 receptor. The absence of competition between ALCAM and T1h suggests that the binding domains for the two are different, as shown in FIG. 8.

Example 3

Lymphocyte Proliferation Inhibition by Flow Cytometry Using CFSE

PBMCs were harvested and washed in PBS. The cells (7.5×10$^6$) were re-suspended in 1 ml of 2≈M carboxyfluorescein succinimidyl ester (CFSE) concentration in PBS. Cells were incubated for 10 minutes exactly at 37éC. 10 ml of Roswell Park Memorial Institute medium (RPMI), 10% FBS was added to stop the reaction. Cells were washed twice with 10 ml of PBS. The cell preparation was then re-suspended in 5 ml of PBS at a cell density of 1.5×10$^6$ cells/ml and 200 ul was added to each BD FACS tube. 200 ul of required and non specific antibody at various concentrations (50 ug/ml, 25 ug/ml, 12.5 ug/ml and 6.25 ug/ml respectively) were added and incubated for 30 minutes at 37éC. 2 ml of PBS was added to each tube and centrifuged at 1200 RPM for 5 minutes at RT to wash away the unbound antibody. 1 ml of RPMI, 10% FBS was added to the pellet in each tube. 1 ml of PHA 20≈g/ml in RPMI 10% FBS was added to the respective tube to stimulate the proliferation. The total volume in the tube is 2 ml and the final concentration of PHA was 10≈g/ml. The tube was vortexed and incubated for 3 day at 37éC in $CO_2$ incubator. Cells were washed with PBS and spun down at 1200 RPM at 4éC for 5 minutes. Supernatant were discarded and resuspended in 500 ul of 1×PBS. Total 20000 events were acquired at around 200 events/sec and viewed in the FITC channel.

% of Inhibition={[PHA−(T1h+PHA)]/PHA}*100

(Where PHA=PHA-cells alone PHA+T1h=(PHA+T1h)-Cells alone
PHA+hR3=(PHA+hR3)−Cells alone
Cells alone is CFSE+cells.

Figure 9:
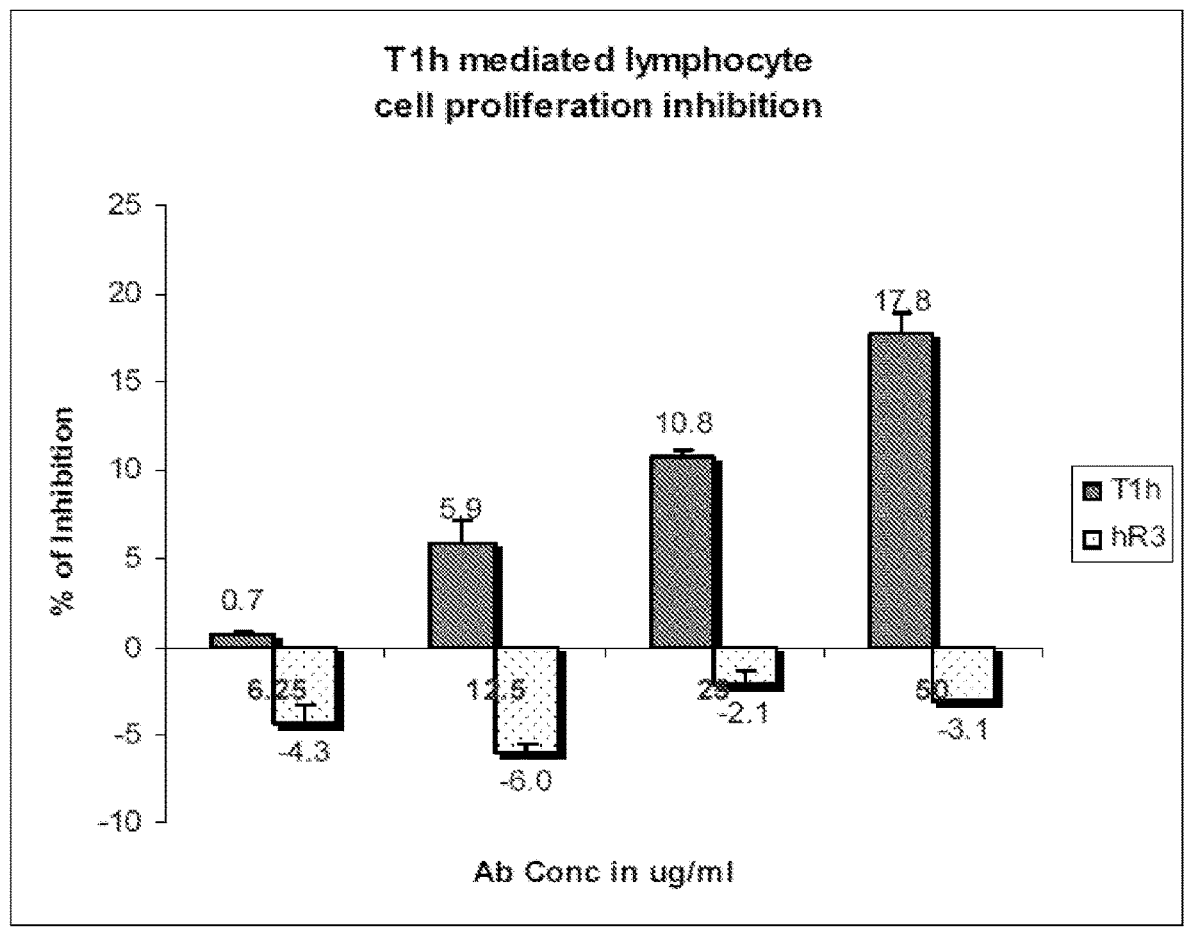
FIG. 9 shows dose dependent inhibition of T1h on lymphocytes as a bar graph. The figure represents the % of inhibition of T1h on PHA activate lymphocytes at various concentration (50 ug/ml, 25 ug/ml, 12.5 ug/ml, 6.25 ug/ml). hR3 (non specific antibody) was used at the same concentration.

These data suggest that T1h antibody mediates the inhibition of proliferation of PHA stimulated lymphocytes in a dose dependent manner. The percentage of inhibition may be varied among the individuals due to inherent variation among normal individuals. However overall, a dose dependent inhibition of PHA stimulated lymphocytes was observed with T1h but not with a nonspecific antibody hR3, as shown in FIG. 9.

Example 4

T1h does not Mediate Complement Dependent Cytotoxicity (CDC)

The Alamar Blue (Resazurin) based assay is used to measure the ability of an antibody to promote cell killing. This is induced by the binding of the antibody to a cell surface antigen thereby fixing and activating complement resulting in target cell lysis. Resazurin is a redox-active dye which when reduced, changes color from blue to pink.

Figure 10:
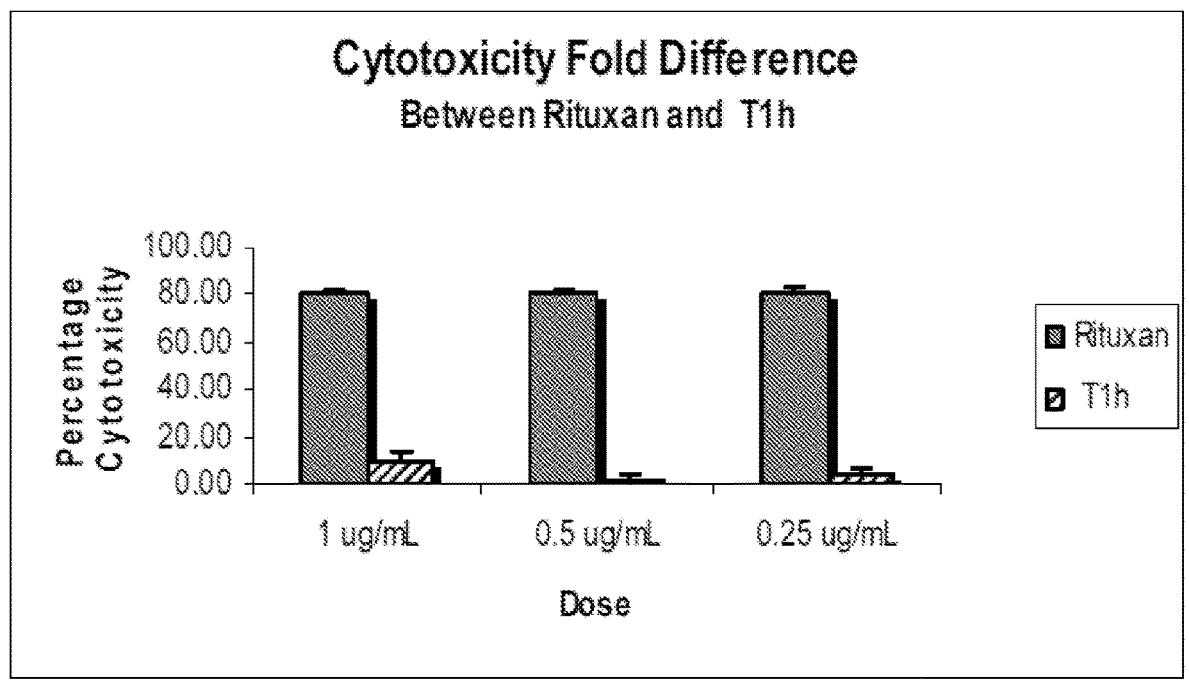
FIG. 10 shows the cytotoxicity fold difference between Rituxan and T1h in CDC assay using Alamar Blue.

Pooled human serum (minimum three) from whole blood was collected in sterile tube the blood was allowed to clot at room temperature for at least 4 hours and is centrifuged at 900 g for 20 minutes. The serum was harvested; aliquoted and stored at −80éC. Target cells (Wil-2S/HUT-78) were washed in dilution buffer and resuspended to $2×10^5$ cells/mL. Antibody was diluted in dilution buffer at 4× of the final desired concentration. Complement was diluted at 4× the desired final concentration (i.e. 1:2.5 dilutions for a final concentration of 1:10). 50≈L each of diluted antibody, diluted complement and 50≈L of cell suspension (10,000 cells/well) were added to each well of a 96-well flat-bottom plate. The following control wells were included: target cells+Ab alone (spontaneous cell death), target cells+serum only (background lysis), and targets cells+10% SDS (for maximum cell death). The positive control was Wil-2S cells treated with Rituxan at different concentrations. 96-well plate was incubated for 2 hours at 37éC. 50 uL/well of Alamar Blue was added to each well, and the plate was incubated overnight at 37éC. Fluorescence was measured on a spectrophotometer Biotek Synergy™. HT with 530 nm excitation, 590 nm emission, and sensitivity=35. The results suggest that T1h does not induce CDC as compared to Rituxan, as shown in FIG. 10. Thus, the results from this experiment conclusively proves that the anti-CD6 monoclonal antibody does not induce CDC in a cell line expressing CD6 namely HUT 78.

Example 5

T1h does not Induce Apoptosis in HUT 78 Cells

One of the hall marks of apoptosis is the translocation of phosphotidylserine (PS) from the inner part of the plasma membrane to the outside. The analysis of phosphotidylserine on the outer leaflet of apoptotic cell membranes is performed by using Annexin-V-Fluorescein and Propidium iodide (PI) for the differentiation of apoptotic and necrotic cells. Annexin V is a $Ca^{2+}$ dependent phospholipid binding protein with a high affinity for phosphotidylserine. While PI binds to distinct necrotic cells, Annexin-V-Fluorescein binds to apoptotic cells. This method helps in distinguishing the apoptotic and necrotic cell populations. The early apoptotic population is only Annexin V positive while the late apoptosis is both Annexin V and PI positive.

The cells were harvested and 1.5 ml of $3.3×10^5$ cells/ml (final cells: $5×10^5$ cells) was seeded in each 35 mm dish. Required amount of antibody was added to respective dishes to make a final concentration of (5≈g/ml). In the control dish, no antibody was added. As a positive control cells were incubated with rapamycin at a concentration of 1.2≈g/ml. Cells were incubated overnight at 37éC in 5% $CO_2$ incubator. The cells were then transferred to FACS tube BD Falcon Cat No: 352054 and centrifuged at 1200 RPM for 5 minutes at Room temperature (RT). The supernatant was discarded and resuspended in 2 ml of PBS and centrifuged at 1200 RPM for 5 mints at RT. The supernatant was discarded and 100≈l of Annexin-V-Fluorescein labeling solution was added and incubated for 10-15 min at RT. The cells were washed with 2 ml of PBS and centrifuged at 1200 RPM for 5 minutes. The supernatant was then discarded. Cells were resuspended in 0.5 ml of PBS and acquired by flow cytometer (3000 cells were gated) with 488 nm excitation. Samples were read in FITC channel for Annexin V and PE Texas red channel for PI. Annexin V alone and PI alone samples in the rapamycin treated arm, were run to enable compensation.

Figure 11:
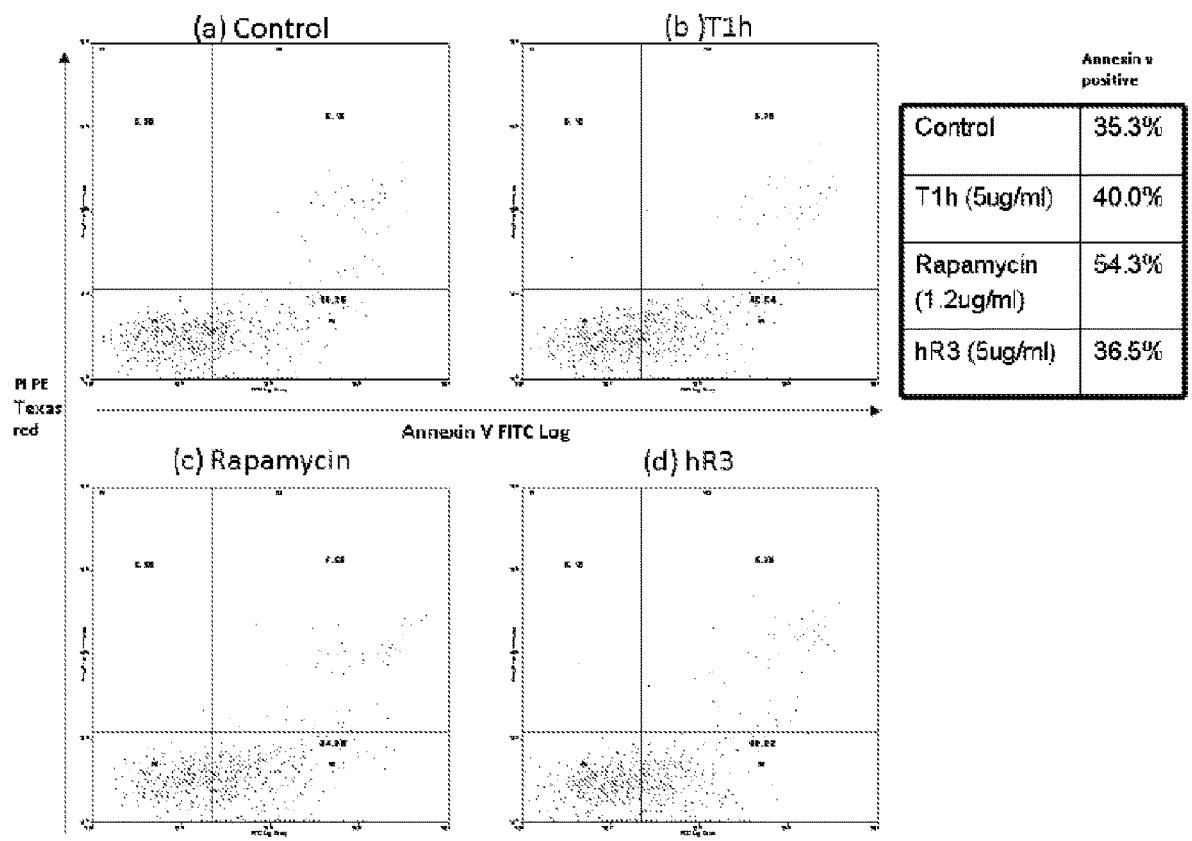
FIG. 11 shows the results of HUT 78 cells treated with T1h antibody (5 ug/ml), hR3 antibody (5 ug/ml), and rapamycin (1.2 ug/ml) or without antibody (as control) that were incubated overnight at 37é in a $CO_2$ incubator. Cells were then treated with Annexin V labeling solution followed by flow cytometry analysis. Annexin V FITC log on horizontal axis, PI/PE texas red on vertical axis.

The HUT 78 cells that were treated with the T1h showed 40% of apoptosis which is almost equal to the untreated control in the Annexin V FITC channel. The untreated and the nonspecific antibody (hR3 antibody) treated cells showed 35.3% and 36.5% apoptosis respectively while the positive control rapamycin showed 54.3% apoptosis. This data suggest that the T1h does not mediate apoptosis in the HUT 78 cells, as shown in FIG. 11.

Example 6

No Inhibition of Memory T-Cells by T1h in a Tetanus Toxoid Mediated T-Cell Proliferation Assay PBMCs were isolated by Ficoll-Paque (Amersham Cat No: 17-14403-03), density gradient centrifugation. Buffy coats were obtained from healthy donors and always harvested fresh. PBMCs were then washed in PBS (Invitrogen). The PBMCs were then re-suspended in 2 ml of RPMI media with 5% FBS supplemented at a cell density of $0.3×10^6$ cells/ml. The cells were then incubated for 30 minutes with or without the T1h 10 ug/ml and hR3 which is used as nonspecific control in a sterile BD FACS 5 ml tube. After incubation, cells were vortexed and 100≈l of the cell suspension was added to the respective wells. 100 ul of the Tetanus toxoid (Cat #582231, CALBIOCHEM) (10 ug/ml) working solution (RPMI media with 5% FBS) was added to the respective wells to stimulate the memory T-cell proliferation. The plates were incubated for five days in the $CO_2$ incubator at 37éC. 65≈l of Alamar blue was added to each well and incubated overnight in a $CO_2$ incubator at 37éC. Fluorescence was measured on a spectrophotometer Biotek Synergy™. HT with 530 nm excitation, 590 nm emission, and sensitivity=35.

Figure 12:
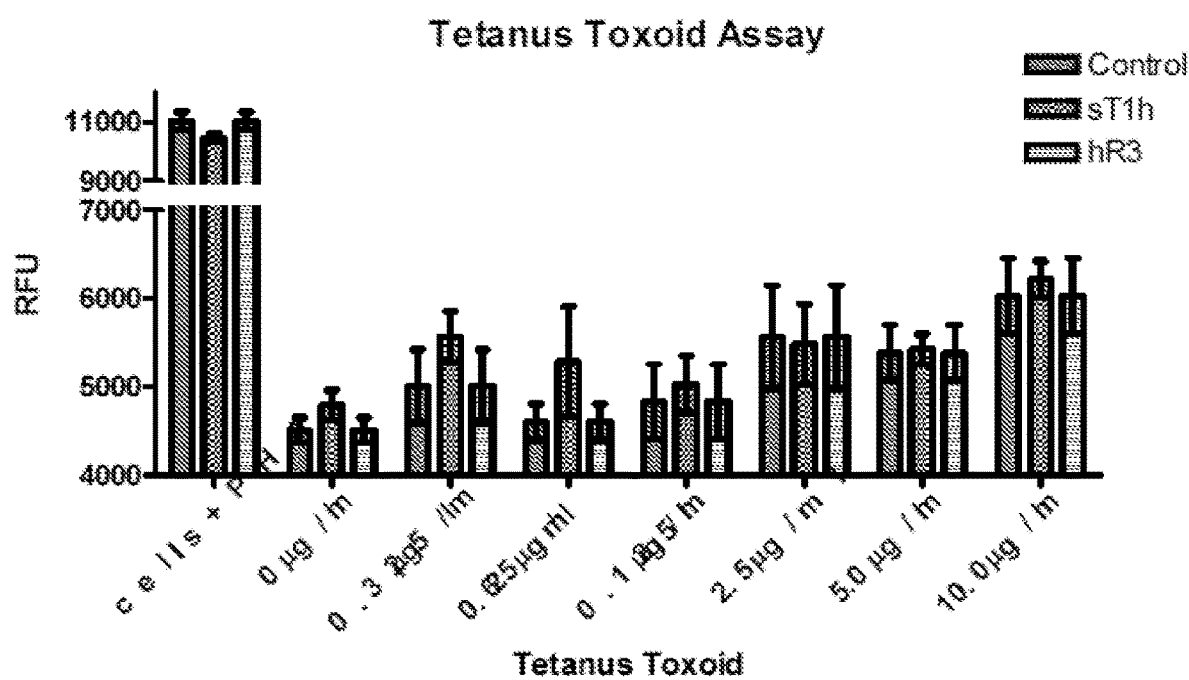
FIG. 12 shows the results of treating PBMCs with T1h antibody (10 ug/ml), hR3 (isotype control) or without antibody (as control) and incubated for 5 days at 37éC in a $CO_2$ incubator. Cells were stimulated with the Tetanus toxoid before incubation. The proliferation was measured with Alamar blue dye. No inhibition of proliferation was observed in the presence of T1h.

The experimental results as set forth in FIG. 12 show that Tetanus Toxoid does stimulate the proliferation of T-cells in a dose dependent manner, but the T1h does not show any inhibition of proliferation of these cells. T his strongly suggests that T1h does not inhibit memory T-cell proliferation. This is favorable for T1h therapy because circulating memory T-cell proliferation is not affected and patients on T1h therapy would not become susceptible to infection.

Example 7

Figure 13:
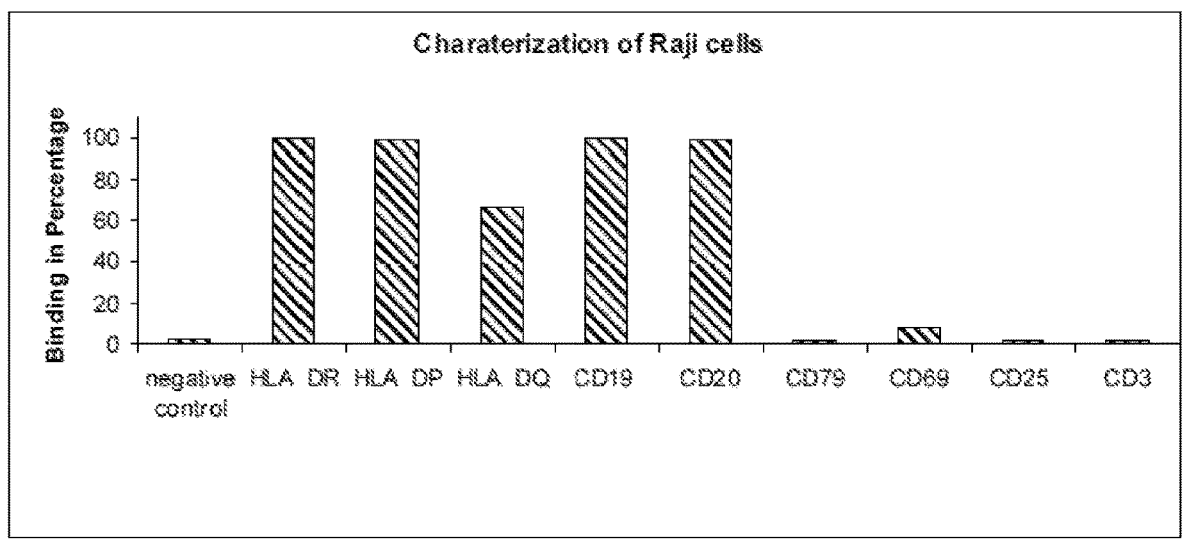
FIG. 13 shows that Raji cells are by immunofluorescence to be true B cells and also express MHC II antigens.
Figure 14:
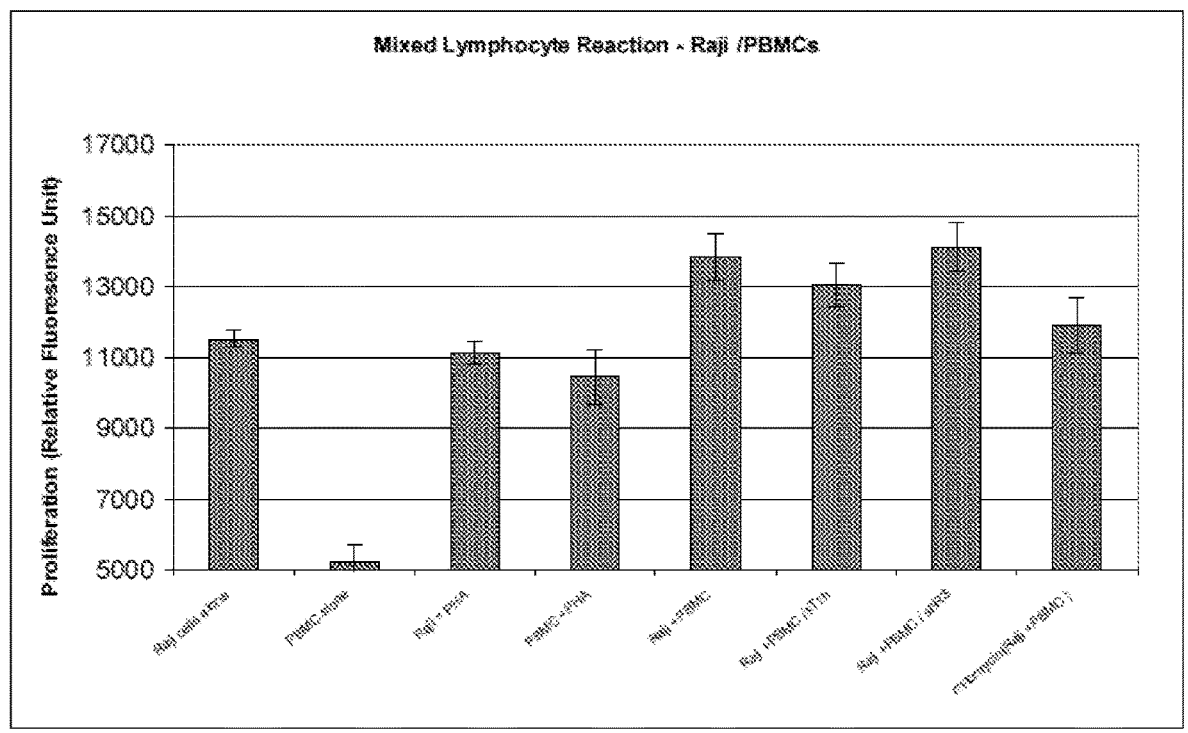
FIG. 14 shows PBMCs proliferative in presence of mitomycin treated Raji cells. Positive control shows that PBMCs grow in presence of PHA. sT1h inhibits T-cell proliferation (significantly by t test) as compared to no antibody or hR3 controls. Each experiment is a mean and standard deviation obtained from six different wells.

T1h Inhibits T-Cell Proliferation in a Mixed Lymphocyte Reaction Mediated by PBMCs and Raji Cells Raji/PBMCs cells were harvested and resuspended in 1×PBS. $8\times10^5$ cells/ml of Raji cells/PBMCs were resuspended in 1 ml of mitomycin (25 ug/ml). Cells were incubated for 30 minutes in a $CO_2$ incubator at 37éC. After Incubation 2 ml of RPMI with 5% FBS was added to each tube and centrifuged at 1200 RPM for 5 minutes at RT to remove the mitomycin. The supernatant was discarded and again 2 ml of RPMI with 5 FBS was added and centrifuged. Supernatant was discarded and cells are resuspended in the RPMI media 50 ul of PBMCs ($4\times10^5$ cells/ml) was added to the respective wells of 96 well round bottom plates. 100≈l of antibody dilution T1h or hR3 (10 ug/ml) was added to the respective wells and incubated for 30 minutes in a $CO_2$ incubator at 37éC. 50 ul of the Mitomycin treated Raji cells ($4\times10^5$ cells/ml) was added into the respective wells. Along with the assay, controls which were included were Mitomycin treated Raji cells alone, PBMCs alone, Mitomycin treated Raji cells+PHA, PBMCs+PHA, Mitomycin treated Raji and PBMCs. The plate was incubated for 5 days in a $CO_2$ incubator at 37éC. 65≈l of Alamar blue was added to each well and incubated overnight in a $CO_2$ incubator at 37éC. Fluorescence was measured on a spectrophotometer Biotek Synergy™. HT with 530 nm excitation, 590 nm emission, and sensitivity=35. In conclusion it was observed, see the results of FIGS. 13 and 14, that T1h can specifically inhibit one way MLR where Raji cells are the Antigen Presenting Cells and PBMCs.

REFERENCES

The contents of all references cited herein are hereby incorporated by reference herein for all purposes.
1. Gangemi et al., Anti-T12, An Anti-CD6 Monoclonal-Antibody, Can Activate Human Lymphocytes-t, J. Immunol. 1989, 143:2439-2447.
2. Bott et al., Activation of Human T-cells Through CD6—Functional-Effects of A Novel Anti-CD6 Monoclonal-Antibody and Definition of 4 Epitopes of The CD6 Glycoprotein, Int. Immunol. 1993, 7:783-792.
3. Morimoto et al., 2h1—A Novel Antigen Involved In Lymphocyte-T Triggering, J. Immunol. 1988, 140:2165-2170.
4. Osorio et al., The Anti-CD6 mab, IOR-t1, Defined a New Epitope on The Human CD6 Molecule That Induces Greater Responsiveness In T-cell Receptor/CD3-Mediated T-cell Proliferation, Cell. Immunol. 1994, 154: 123-133.
5. Swack et al., Structural Characterization of CD6—Properties of 2 Distinct Epitopes Involved In T-cell Activation Structural Characterization of CD6—Properties of 2 Distinct Epitopes involved In T-cell Activation, Mol. Immunol. 1989 26:1037-1049.
6. Swack et al., Biosynthesis And Posttranslational Modification of CD6, a T-cell Signal-Transducing Molecule, J. Biol. Chem. 1991, 266:7137-7143;
7. Cardenas et al., Phosphorylation-Dephosphorylation of The CD6 Glycoprotein Renders 2 Isoforms of 130 and 105 Kilodaltons—Effect of Serum and Protein-Kinase-C Activators, J. Immunol. 1990, 145:1450-1455.
8. Wee et al., Tyrosine Phosphorylation of CD6 By Stimulation of CD3—Augmentation By The CD4 and CD2 Coreceptors, J. Exp. Med. 1993, 177:219-223.
9. Aruffo et al., The Lymphocyte Glycoprotein-CD6 Contains a Repeated Domain-Structure Characteristic Of a New Family Of Cell-surface And Secreted Proteins, J. Exp. Med. 1991, 174:949-952.
10. Wee, et al., Characterization Of A CD6 Ligand(s) Expressed On Human-Derived And Murine-Derived Cell-Lines And Murine Lymphoid-Tissues, Cell. Immunol. 1994, 158:353-364.
11. Patel, et al., Identification And Characterization of A 100-Kd Ligand For CD6 On Human Thymic Epithelial-Cells, J. Exp. Med. 1995. 181:1563-1568.
12. Bowen et al., Cloning, Mapping, And Characterization of Activated Leukocyte-Cell Adhesion molecule (ALCAM), a CD6 Ligand, J. Exp. Med 1995, 181:2213-2220.
13. Whitney, et. al., The Membrane-Proximal Scavenger Receptor Cysteine-Rich Domain of CD6 Contains The Activated Leukocyte Cell-Adhesion Molecule-Binding Site, J. Biol. Chem. 1995, 270: 18187-18190.
14. Gimferrer I. Relevance of CD6-mediated interactions in T-cell activation and proliferation, J Immunol 2004. 173: 2262-2270.
15. Roque-Navarro L., et al., Humanization of Predicted T-cell Epitopes Reduces the Immunogenicity of Chimeric Antibodies: New Evidence Supporting A simple Method, Hybridoma and Hybridomics 2003.22:245-257.
16. Alonso-Ramirez, R., et al., Rationale for Targeting CD6 as a Treatment for Autoimmune Diseases. Arthritis. 2010: p. 130646.
17. Rodriguez, P. C., et al., A clinical exploratory study with itolizumab, an anti-CD6 monoclonal antibody, in patients with rheumatoid arthritis. Immunol. Results. 2012, 2: p. 204-11.
18. Blank, M. and Y. Shoenfeld, Experimental models of systemic lupus erythematosus: anti-dsDNA in murine lupus. Rheumatology (Oxford), 2005. 44(9): p. 1086-9.
19. Liu, K. and E. K. Wakeland, Delineation of the pathogenesis of systemic lupus erythematosus by using murine models. Adv Exp Med Biol, 2001. 490: p. 1-6.
20. Perry, D., et al., Murine models of systemic lupus erythematosus. J Biomed Biotechnol. 2011: p. 271694.
21. Theofilopoulos, A. N. and F. J. Dixon, Murine models of systemic lupus erythematosus. Adv Immunol, 1985. 37: p. 269-390.
22. Mannoor, K., et al., Expression of natural autoantibodies in MRL-lpr mice protects from lupus nephritis and improves survival. 2012, J Immunol. 188(8): p. 3628-38.
23. Adhya, Z., S. Borozdenkova, and M. Y. Karim, The role of cytokines as biomarkers in systemic lupus erythematosus and lupus nephritis. 2011, Nephrol Dial Transplant. 26(10): p. 3273-80.
24. Marian, V. and J. H. Anolik, Treatment targets in systemic lupus erythematosus: biology and clinical perspective. 2012 Arthritis Res Ther. 14 Suppl 4: p. S3.
25. Poole, B. D., et al., Cytokines in systemic lupus erythematosus. J Biomed Biotechnol. 2010: p. 735169.
26. Richards, H. B., et al., Interleukin 6 dependence of anti-DNA antibody production: evidence for two pathways of autoantibody formation in pristane-induced lupus. J Exp Med, 1998. 188(5): p. 985-90.
27. Li, Y., et al., Anti-DNA B cells in MRL/lpr mice show altered differentiation and editing pattern. J Exp Med, 2002. 196(12): p. 1543-52.
U.S. Pat. No. 6,372,215
U.S. Pat. No. 5,712,120
EP 0699755
U.S. Pat. No. 6,572,857
EP 0807125
PCT/IN2008/00562

The invention claimed is:

1. A method for treating lupus nephritis in a subject in need thereof comprising administering an anti-CD6 monoclonal antibody that comprises amino acid sequences of SEQ ID NO: 1 and SEQ ID NO: 2, and wherein the anti-CD6 monoclonal antibody is in a therapeutically effective amount to reduce the symptoms of lupus nephritis in the treated subject.

2. The method of claim 1, wherein the anti-CD6 monoclonal antibody reduces or prevents the activation of T-cells, inhibits T-cell proliferation and/or reduces induction of complement-dependent cytotoxicity (CDC).

3. The method of claim 1, wherein the anti-CD6 monoclonal antibody is encoded by a nucleotide sequence comprising SEQ ID NO: 3 and SEQ ID NO: 4 or nucleotide sequences have at least 90% identity thereto and encodes for SEQ ID NO: 1 and SEQ ID NO: 2.

4. The method of claim 1, wherein (i) the anti-CD6 monoclonal antibody is administered by parenteral delivery; (ii) the method further comprises combining the anti-CD6 monoclonal antibody with a pharmaceutically acceptable carrier; or, the anti-CD6 monoclonal antibody is combined with a chemotherapeutic agent, an immunosuppressive agent, an anti-malarial drug, a cytotoxic agent, an integrin antagonist, a cytokine antagonist, or a hormone.

5. The method of claim 1, wherein the therapeutically effective amount is about 0.01 to about 100 mg/kg per subject body weight.

6. The method of claim 1, wherein the anti-CD6 monoclonal antibody causes a reduction in pro inflammatory cytokines.

7. The method of claim 1, wherein the subject does not have an autoimmune disease other than lupus.

* * * * *